(12) United States Patent
Paloheimo et al.

(10) Patent No.: US 6,228,629 B1
(45) Date of Patent: May 8, 2001

(54) XYLANASES, GENES ENCODING THEM, AND USES THEREOF

(75) Inventors: Marja Paloheimo, Vantaa; Satu Hakola, Perttula; Arja Mäntylä, Helsinki; Jari Vehmaanperä; Raija Lantto, both of Klaukkala; Tarja Lahtinen, Vantaa; Richard B. Fagerström, Espoo; Pirkko Suominen, Helsinki, all of (FI)

(73) Assignee: Röhn Enzyme Finland OY, Rajamäki (FI)

( * ) Notice: Subject to any disclaimer, the term of this patent is extended or adjusted under 35 U.S.C. 154(b) by 0 days.

(21) Appl. No.: 08/768,373

(22) Filed: Dec. 17, 1996

Related U.S. Application Data

(60) Provisional application No. 60/020,389, filed on Jun. 28, 1996, and provisional application No. 60/008,746, filed on Dec. 18, 1995.

(51) Int. Cl.[7] .................. C12N 9/00; C12N 9/24; D21C 1/00; C12P 19/14
(52) U.S. Cl. ............... 435/200; 435/183; 435/99; 435/277; 435/278; 426/53; 426/622; 426/635; 426/549
(58) Field of Search ............... 455/200; 435/183, 435/200, 99, 277, 278; 426/53, 622, 635, 549

(56) References Cited

U.S. PATENT DOCUMENTS 5,298,405   3/1994   Nevalainen et al. ............... 435/209

FOREIGN PATENT DOCUMENTS

| 2154945 | 1/1996 | (CA) . |
| 0 406 617 | 1/1991 | (EP) . |
| 2-119790 | 5/1990 | (JP) . |
| WO 91/05908 | 5/1991 | (WO) . |
| WO 93/19171 | 9/1993 | (WO) . |
| WO 93/24621 | 12/1993 | (WO) . |
| WO 95/12668 | 5/1995 | (WO) . |
| WO 96/23062 | 8/1996 | (WO) . |

OTHER PUBLICATIONS

Alconada, T.M. and M.J. Martinez, "Purification and characterization of an extracellular endo–1,4–β–xylanase from *Fusarium oxysporum* f. sp. *melonis*," *FEMS Microbiol. Lett.* 118(3):305–310 (May 1994).

Aono, R., "Thermostable Alkaline Xylanases Produced by Alkaliphilic Strains of *bacillus* spp.," *Kami Pa Gikyoshi* 48(9):1148–1166 (1994).

Bailey, M.J. et al., "Interlaboratory testing of methods for assay of xylanase activity," *J. Biotechnol.* 23(3):257–270 (1992).

Bajpai, P. and P.K. Bajpai, "Biobleaching of Kraft Pulp," *Process Biochem.* 27(6):319–325 (1992).

Christakopoulos, P. et al., "Purification and characterization of two low molecular mass alkaline xylanases from *Fusarium oxysporum* F3," *J. Biotechnol.* 51(2):181–189 (Nov. 1996).

Dubeau, H. et al., "Xylanase of *Chaetomium cellulolyticum*: Its Nature of Production and Hydrolytic Potential," *Biotechnol. Lett.* 9(4):275–280 (1987).

Farrell, R.L., et al., "New bleach sequences of kraft pulp using white white–rot fungi," in *Ligno–cellulosics: Science, Technology, Development and Use*, Kennedy, J.F. et al., Eds, E. Horwood; New York, pp. 305–315 (1992).

Gandhi, J.P., et al., "Characterization of Extracellular Thermostable Xylanase From *Chaetomium globosom*," *J. Chem. Tech. Biotechnol.* 60(1):55–60 (May 1994).

Ganju, R.K. et al., "Purification and characterization of two xylanases from *Chaetomium thermophile* var. *coprophile*," *Can. J. Microbiol.* 35:836–842 (1989).

Gilkes, N.R. et al., "Domains in Microbial α–1,4–Glycanases: Sequence Conservation, Function, and Enzyme Families," *Microbiological Rev.* 55(2):303–315 (1991).

Irie, T. et al., "Purification of xylanase from *Chaetomium gracile* Mutant 1161 and its xylobiose–forming properties," *Hakkokogaku* 70(2):109–114 (1992).

Jurasek, L., "Direct biological bleaching of pulps," in *Ligno– cellulosics: Science, Technology, Development and Use*, Kennedy, J.F. et al., Eds, E. Horwood; New York, pp. 317–325 (1992).

Kantelinen, A. et al., "Hemicellulases and Their Potential Role in Bleaching," in Tappi Proceedings: 1988 Intl. Pulp Bleaching Conf., Jun. 5–9, Orlando, pp. 1–9 (1988).

Karhunen, T. et al., "High frequency one–step gene replacement in *Trichoderma reesei*. I. Endoglucanase I overproduction," *Mol. Gen. Genet.* 241(5–6):515–522 (1993).

Kawaminami, T. and H. Iizuka, "Studies on Xylanase from Microorganisms. (IV) Action of Xylanase of *Chaetomium trilaterale* Strain No. 2264 upon Xylan," *J. Ferment. Technol.* 48(3):161–168 (1970).

Onysko, K.A., "Biological Bleaching of Chemical Pulps: A Review," *Biotech. Adv.* 11:179–198 (1993).

Rajaram, S. and A. Varma, "Production and characterization of xylanase from *Bacillus thermoalkalophilus* grown on agricultural wastes," *Appl. Microbiol. Biotechnol.* 34:141–144 (1990).

Senior, D.J. and J. Hamilton, "Use of Xylanases to Decrease the Formation of AOX in Kraft Pulp Bleaching," *J. Pulp Paper Sci.* 18(5):J165–J169 (1992).

(List continued on next page.)

Primary Examiner—Rebecca E. Prouty
Assistant Examiner—Manjunath Rao
(74) Attorney, Agent, or Firm—Sterne, Kessler, Goldstein & Fox P.L.L.C.

(57) ABSTRACT

DNA encoding novel xylanases, vectors containing such DNA, hosts transformed with such DNA, enzyme preparations, and the use of such preparations are described.

16 Claims, 14 Drawing Sheets

OTHER PUBLICATIONS

Viikari, L. et al., "Bleaching With Enzymes," Proceedings of 3rd Intl. Conf. on Biotech. in the Pulp and Paper Indust., Stockholm, pp. 67–69 (1986).

Viikari, L. et al., "Application of Enzymes in Bleaching," in Proceedings of 4th Intl. Symp. on Wood and Pulping Chem., Paris, pp. 151–154 (1987).

Viikari, L. et al., "Xylanase," *Paper and Timber* 73(5):384–389 (1991).

Viikari, L. et al., "Hemicellulases for Industrial Applications," in *Bioconversion of Forest and Agricultural Plant Residues*, Saddler, J.N., Ed; CAB International, Wallingford, pp. 131–182 (1993).

Viikari, L. et al., "Xylanases in bleaching: From an idea to the industry," *FEMS Microbiol. Rev.* 13(1):335–350 (Jan. 1994).

Wong, K.K.Y. et al., "Multiplicity of β–1,4–Xylanase in Microorganisms: Functions and Applications," *Microbiological Rev.* 52(3):305–317 (1988).

Yoshino, S. et al., "Two family G xylanase genes from *Chaetomium gracile* and their expression in *Aspergillus nidulans*," *Curr. Genet.* 29(1):73–80 (Dec. 1995).

GenBank report for EMBL search, Accession No. Z49892, from Perez–Gonzalez J.A. et al., "*A. nidulans* gene for xylanase," submitted Jun. 1995.

GenBank report for NCBI Entrez search, Accession No. D49850, from Tsukagoshi, N., "*Chaetomium gracile* endo–beta1,4–xylanase A (cgxA) gene, complete cds," submitted Mar. 1995.

GenBank report for NCBI Entrez search, Accession No. D49851, from Tsukagoshi, N., "*Chaetomium gracile* endo–beta1,4–xylanase B (cgxB) gene, complete cds," submitted Mar. 1995.

GenBank report for NCBI Entrez search, Accession No. L25310, from Stalbrand H. et al., "*Trichoderma reesei* beta–mannanase mRNA, complete cds," submitted 1993.

GenPept report for NCBI Entrez search, Accession No. A44595, from Yaguchi, M., "endo–1,4–beta–xylanase (EC 3.2.1.8) IIB (proteinase–sensitive)–fungus (*Trichoderma viride*)," submitted Mar. 1994.

English language abstract of Japanese Patent No. 2–119790, Dialog WPI Acc. No. 90–182390/199024.

Grant, R., "R&D optimizes enzyme applications," *Pulp and Paper Intl.*, pp. 56–57, Sep. 1993.

Pérez–González, J. A. et al., "Molecular Cloning and Expression in *Saccharomyces cerevisiae* of Two *Aspergillus nidulans* Xylanase Genes," *Appl. Environ. Microbiol.* 62(6):2179–2182 (Jun. 1996).

```
-194   actgtctagatgcaactatacccagcagaggttgtgatcgagctcaagtctaaacttgga

-134   agaagcacccagaggacaggtttggaggacctctcacgaatacataaaggcctcaagacc

-74    tctcccagagcttcctctactcctttcatcttcaccgaccgtgatacaaacagaaaatag

-14    catcatatatcaagATGGTCAACTTCTCAACTCTCTTCCTCGCGGCTTCGACCGCAGCAC
                  M  V  N  F  S  T  L  F  L  A  A  S  T  A  A  L 47     TTGCTGCTGCTGCCCCCAGCATCGAGAAGCGTCAGACGCTCACCAGCAGTGCCACCGGCA
       A  A  A  A  P  S  I  E  K  R  Q  T  L  T  S  S  A  T  G  T
             ↑

107    CCCACAATGGCTACTACTACAGCTTCTGGACCGATGGCCAAGGCAACATTCGCTTCAACC
       H  N  G  Y  Y  Y  S  F  W  T  D  G  Q  G  N  I  R  F  N  L

167    TCGAGAGCGGTGGCCAGTACAGCGTGACATGGTCTGGTAACGGCAACTGGGTTGGCGGCA
       E  S  G  G  Q  Y  S  V  T  W  S  G  N  G  N  W  V  G  G

227    AAGgtatgtctctttaatgtttccagcgctatggaatgaactaaatgctaacctgttaac
       G 287    agGCTGGAACCCCGGTACCGATAACCGTGTCATCAACTACACAGCCGACTACAGACCCAA
          W  N  P  G  T  D  N  R  V  I  N  Y  T  A  D  Y  R  P  N 347    CGGCAACTCCTACCTCGCCGTCTACGGCTGGACCCGCAACCCGCTGATCGAGTACTACGT
       G  N  S  Y  L  A  V  Y  G  W  T  R  N  P  L  I  E  Y  Y  V 407    GGTCGAGAGCTTCGGCACTTACGACCCGTCGACGGGCGCCACCCGCATGGGCAGCGTGAC
       V  E  S  F  G  T  Y  D  P  S  T  G  A  T  R  M  G  S  V  T 467    CACCGACGGCGGCACCTACAACATCTACCGCACGCAGCGCGTCAACGCGCCCTCCATCGA
       T  D  G  G  T  Y  N  I  Y  R  T  Q  R  V  N  A  P  S  I  E 527    GGGCACCAAGACCTTCTACCAATACTGGTCTGTGCGCACCTCCAAGCGCACCGGCGGTAC
       G  T  K  T  F  Y  Q  Y  W  S  V  R  T  S  K  R  T  G  G  T 587    TGTTACCATGGCCAACCACTTCAATGCTTGGAGGCAGGCTGGTCTGCAGCTGGGTTCCCA
       V  T  M  A  N  H  F  N  A  W  R  Q  A  G  L  Q  L  G  S  H 647    TGATTATCAGATTGTGGCTACTGAGGGTTACTACTCGTCTGGCTCGGCGACTGTCAATGT
       D  Y  Q  I  V  A  T  E  G  Y  Y  S  S  G  S  A  T  V  N  V 707    TGGCGGCAGCACTACTGGTGGTAACAATGGCGGTAACAATGGCGGTAACAATGGCGGTAA
       G  G  S  T  T  G  G  N  N  G  G  N  N  G  G  N  N  G  G  N 767    CAATGGCGGCAACACTGGCTCGAACGTGAGTATCTCCAGACCCCGCAAGATGGGAAGTTT
       N  G  G  N  T  G  S  N  V  S  I  S  R  P  R  K  M  G  S  L 827    AGCCAGTACAAGAAGCTAAcaagcatgcagtgctctcctatttggggtcagtgcggcggc
       A  S  T  R  S  *

887    cagggctggaccggcccgacctgctgccagagcggctcgacctgccgcttccagaacaac 947    tggtactctcagtgcctgtaaattttcgaacttcatcacaagcatccgccaaattctgtc 1007   gtcgtcaaatcacgcaggcttgggaactttttatctcatgtcctgggccaggacgcagga 1067   gttaggacccggatgaggcct
```

FIG. 2

```
-203    ggggagggtgcctgatgtttgttgcttatggatcactgggtcgggatgtagaagatatac

-143    aacttaagggcgctgttatggcagcacgacatcaaagtatataaaccggtagccatcttc

-83     ctagctcgagaatcattgacctcaccgtccagctccccactgcagtcctctctccaacca

-23     caggacatcagacaacgatcaccATGGTCTCCCTCAAATCCCTCCTCCTCACAGCCGCCA
                                M  V  S  L  K  S  L  L  L  T  A  A  T 38      CTGCCCTGGCATTCCCTCTCGAGGCATTCAACGCCACCGAGGGTTTCAATGCCACATCTC
         A  L  A  F  P  L  E  A  F  N  A  T  E  G  F  N  A  T  S  L
                  ↑

98      TCCACGAGCTGATGGTCCGAGCTGGCACCTCCAGCGGCACGGGCACACACAACGGGTGGT
         H  E  L  M  V  R  A  G  T  S  S  G  T  G  T  H  N  G  W  Y

158     ATTACTCCTTCTGGACCGACGGCGGCGGCACGGTGTGGTACACCAATGGTAATGGCGGGT
         Y  S  F  W  T  D  G  G  G  T  V  W  Y  T  N  G  N  G  G  S

218     CGTATAGTGTGAACTGGCAGAACTGTGGAAATTTTGTCGGCGGAAAGGGATGgtaagctc
         Y  S  V  N  W  Q  N  C  G  N  F  V  G  G  K  G  W 278     actgtccacccggacactgaaacttagtgccgagccagatgctgacctctgtccagGCGC
                                                                  R 338     ACCGGCGCAGCCGCAACGATCAAATACTCCGGCAACTACAACCCGTCCGGCAACAGCTAC
         T  G  A  A  A  T  I  K  Y  S  G  N  Y  N  P  S  G  N  S  Y 398     CTCGCCATCTACGGCTGGACGCGCAACCCCCTGGTTGAGTACTACATCGTCGAGTCGTAC
         L  A  I  Y  G  W  T  R  N  P  L  V  E  Y  Y  I  V  E  S  Y 458     GGCACTTACGATCCGTCGTCGGGCGCCCAGAACTTGGGCACATTCCAGTCGGACGGCGGG
         G  T  Y  D  P  S  S  G  A  Q  N  L  G  T  F  Q  S  D  G  G 518     ACGTACAAGATCGCCAAGAGCACGCGGTACAATGCTCCCTCAATCGAAGGAACCAAGACG
         T  Y  K  I  A  K  S  T  R  Y  N  A  P  S  I  E  G  T  K  T 578     TTTACGCAGTATTGGAGCGTGAGGACGTCAAAGCGGGTTGGAGGCACGGTGACGGTTGCG
         F  T  Q  Y  W  S  V  R  T  S  K  R  V  G  G  T  V  T  V  A 638     AACCATTTCAATGCTTGGAAGAGTAAGGGGTTGAATTTGGGTAGCCACGATTATCAGATT
         N  H  F  N  A  W  K  S  K  G  L  N  L  G  S  H  D  Y  Q  I 698     GTGGCGACTGAGGGTTATAAGAGTAGTGGGTCGGCTTCGATTACTGTTCAGTCTGGTTGA
         V  A  T  E  G  Y  K  S  S  G  S  A  S  I  T  V  Q  S  G  *

758     gtgaagcgagatctgggggagagaaacagcgtagagggatgtcagggttcaaggtctggg 818     gaacaaggcttcactcaccgaggtgcggtcggggatgagctactgcaacttctgcagatt 878     agcaactgtttaggtagttgatgggcagaatataccagtcattctggagatatatatcat 938     tgatttcaaacctatatctgggaccggcctcgag
```

FIG. 3

-168    ggcagcagagacgtcgggctaatgtgttgaggtgatgcgacatggtgaaacagggggga

-108    gataaaagagactcgacttttctttaagcacaaaagacatcacgatccgtgaagccctaa

-48     ctgcacactattgacaagttcaccaacgccacacttccaatcctcacaATGGTCAAACTC
                                                         M  V  K  L 13      GCCCTCCTCACAACCTCCCTCCTCACCTCTGGCGCCCTCACCTCCCCAGTCTCAAACCCA
        A  L  L  T  T  S  L  L  T  S  G  A  L  T  S  P  V  S  N  P
                                              ↑

73      AACCGCCCTCCCTCTCGAGACATCTCCCCCCGCCAATGGGGCGGCGGAGGCTACTACTTC
        N  R  P  P  S  R  D  I  S  P  R  Q  W  G  G  G  Y  Y  F

133     CAAAACTGGTCCGAAGGTGGCAGCAACGTGCGCTGCGTGAACGGCCCCAGGCGGGCAATTC
        Q  N  W  S  E  G  G  S  N  V  R  C  V  N  G  P  G  G  Q  F

193     AGCGCGACCTGGAACAGCAAGGGTGGGTTCGTGTGCGGTAAGGGCTGGTCGGCGGGTGGT
        S  A  T  W  N  S  K  G  G  F  V  C  G  K  G  W  S  A  G  G

253     GCACGgtaactacattccccccctctccccccttatccctacctaccgccccaacgaaaa
        A  R 313     caagactaacgagctatagAGTAATCACCTACTCCGGCACCTACAACGCCACGGGGCCCG
                           V  I  T  Y  S  G  T  Y  N  A  T  G  P  G 373     GCTACCTCGCCGTCTACGGATGGACTCGCAACCCCTTGATCGAGTACTACATCATCGAAG
         Y  L  A  V  Y  G  W  T  R  N  P  L  I  E  Y  Y  I  I  E  A 433     CACATGCCGAACTTTCCCCCAACGAGCCCTGGACCTACATGGGTAACTTTTCTTCTCCCG
         H  A  E  L  S  P  N  E  P  W  T  Y  M  G  N  F  S  S  P  E 493     AAGGAGACTACGACATCTACACCAGCTGGCGCATCAATAAGCCGTCGATTGAGGGGACAC
         G  D  Y  D  I  Y  T  S  W  R  I  N  K  P  S  I  E  G  T  R 553     GAACGTTCCAACAGTTCTGGAGCGTGCGAAAGGAACAGAGGGTTAGCGGAACGGTGACCA
         T  F  Q  Q  F  W  S  V  R  K  E  Q  R  V  S  G  T  V  T  T 613     CACAGAGGCATTTTGATGAGTGGGCTAAGCTGGGGATGCGGCTGGGGAGGCATGATTATG
         Q  R  H  F  D  E  W  A  K  L  G  M  R  L  G  R  H  D  Y  V 673     TGGTGATGGCGGTCGAGGGGTATACGGCTGATGGGGGGTGGGGGAGTGCAGGGGAGGCGA
         V  M  A  V  E  G  Y  T  A  D  G  G  W  G  S  A  G  E  A  T 733     CGATTACGGTGCAGTGAaggattggatggggtgagtaaggaacctgggtgataggtgagg
         I  T  V  Q  *

793     ctcccaggatgggggaggatggaggtggaggaactcgacgggtttgggcccagttgagtc 853     acaacagaggcagttatggtagtagagaaataccagtacaatatattctaccaaaccgtg 913     ttaagcacgaaaagtccccctttgctggcatcgcgggccatccagatgttgcaaccttca 973     gc

FIG. 4

XYLANASES, GENES ENCODING THEM, AND USES THEREOF

This application claims the benefit of U.S. Provisional application No. 60/020,389 filed Jun. 28, 1996 and No. 60/008,746 filed Dec. 18, 1995

BACKGROUND OF THE INVENTION

1. Field of the Invention

The present invention is related to genes encoding novel xylanases and compositions containing the novel xylanases. These compositions are especially useful in pulp and paper industries and in modifying plant biomass, like as feed additive or in baking.

2. Description of Related Art

Plant biomass is a composite material consisting primarily of a matrix of cellulose, hemicellulose, and lignin. Enzymes degrading e.g. the hemicellulose xylan, xylanases, can be used e.g. in animal feed compositions which are rich in arabinoxylans and glucoxylans, in baking, and in pulp and paper applications, e.g. to improve the bleachability of pulps.

Thus, when added to feeds (e.g. for monogastric animals, e.g. poultry or swine) which contain cereals (e.g. barley, wheat, maize, rye or oats) or cereal by-products, a hemicellulolytic enzyme improves the break-down of plant cell walls which leads to better utilization of the plant nutrients by animal. This leads to improved growth rate and feed conversion. Also, the viscosity of the feeds containing xylan can be reduced.

In baking applications small amounts of xylanases added to the flour impart favorable characteristics to the dough and to the bread itself. Such characteristics include e.g. increased loaf volume and better textural characteristics (break and shred quality and crumb quality).

In the pulp and paper industry xylanases and other hemicellulases are used, e.g., to improve the bleachability of the pulp.

The aim of kraft pulp bleaching is to remove the residual lignin that is left in pulp after kraft cooking. Traditionally, this has been done using chlorine-containing chemicals. Because of environmental concerns and consumer demands, alternative bleaching technologies have been desired.

The first biotechnical approach to this problem was to attack the lignin directly with lignin degrading enzymes. However, the chemistry of enzymatic lignin degradation seems to be very complicated and difficult to control.

Lignin can be degraded, if the whole microorganism that produces ligninases is used. However, treatment times are relatively long. For example, treatment times may take days, and the microorganisms need supplemental nutrients to work. It can also be difficult to control the growth of other, undesired, microbes. Lignin degradation by using ligninases or by microorganisms is the subject of much research. (see, for example, Farrell, R. L. et al., Lignocellulosics 305–315 (1992); Jurasek, L., Lignocellulosics 317–325 (1992)).

In addition to cellulose and lignin, wood pulp contains hemicellulose. Another approach to lignin removal is to attack hemicellulose—the third main component of wood. The hemicellulose in native hardwood is mainly xylan, while in softwood the hemicellulose is mainly glucomannans and some xylan. During kraft cooking, part of the xylan is dissolved into the cooking liquor. Towards the end of the cooking period when the alkali concentration decreases, part of the dissolved and modified xylan reprecipitates back onto the cellulose fiber. In 1986, it was noticed that xylanase pretreatment of unbleached kraft pulp results in a lessened need for chemicals in the bleaching process (Viikari, L. et al., Proceedings of the 3rd Int. Conf. on Biotechnology in the Pulp Paper Ind., Stockholm (1986), pp. 67–69). Xylanase pretreatment of kraft pulp partially hydrolyses the xylan in kraft pulp. This makes the pulp structure more porous and enables more efficient removal of lignin fragments in the subsequent bleaching and extraction stages. Later, in several laboratories, the xylanase pretreatment was reported to be useful in conjunction with bleaching sequences consisting of $Cl_2$, $ClO_2$, $H_2O_2$, $O_2$ and $O_3$. See reviews in Viikari, L. et al., FEMS Microbiol. Rev. 13: 335–350 (1994); Viikari, L. et al., in: Saddler, J. N., ed., Bioconversion of Forest and Agricultural Plant Residues, C-A-B International (1993), pp. 131–182; Grant, R., Pulp and Paper Int. (September 1993), pp.56–57; Senior & Hamilton, J. Pulp & Paper :111–114 (September 1992); Bajpai & Bajpai, Process Biochem. 27:319–325 (1992); Onysko, A., Biotech. Adv. 11:179–198 (1993); and Viikari, L. et al., J. Paper and Timber 73:384–389 (1991).

As a direct result of the better bleachability of the pulp after such a xylanase treatment, there is a reduction of the subsequent consumption of bleaching chemicals, which when chloride containing chemicals are used, leads to a reduced formation of environmentally undesired organochlorine compounds. Also as a direct result of the better bleachability of pulp after a xylanase treatment, it is possible to produce a product with a final brightness where such brightness would otherwise be hard to achieve (such as totally chlorine free (TCF) bleaching using peroxide). Because of the substrate specificity of the xylanase enzyme, cellulose fibers are not harmed and the strength properties of the product are well within acceptable limits.

However, in many of the practical applications, the use of xylanases is not straightforward; the xylanases must be active in the temperature and pH conditions of the process in which they are used. Formulation of commercial feed using pelleting, extrusion or expanding, often contains steps involving high temperatures (70–180° C.). Enzymes added to the formulation process should withstand these conditions. On the other hand, the corresponding temperature in the intestine of animals is about 40° C. Thus, ideal xylanases for feed compositions should withstand the above mentioned extream temperatures. In bleaching applications, xylanase application is not as simple as adding a xylanase treatment step. Because the bleaching process, and even the sequence of the steps used in the bleaching process varies in different pulp mills, there is thus a continous need to find new xylanases active in different temperature and pH conditions.

Most commercial xylanases designed for feed applications and pulp bleaching are not very thermo-tolerant, especially when neutral or alkaline pH conditions are used. In practice, xylanases are generally inefficient or inactive at temperatures higher than 60° C. and often these enzymes work under acidic conditions. Generally, there are differences in the physical characteristics of xylanases of fungi and bacteria (for review, see Wong et al., Microbiol. Rev. 52:305–317 (1988)). Typically, fungal xylanases have a temperature optimum at about 50° C. and lower pH optimum than have those of bacterial origin. Xylanases of bacterial origin generally have a temperature optimum in the range of 50 to 70° C.

PCT/US90/05933 (WO 91/05908) proposes the use of xylanase in pulp bleaching together with chlorine or chlorine compounds. Chaetomium is proposed as a xylanase source. Screening for xylanase from Streptomyces and Chainia strains is described. Bleaching experiments were performed using xylanase preparations from Chainia sp. culture medium.

EP-A 0 406 617 proposes the use of xylanase in an enzymatic delignifying process of lignocellulosic material, especially after a ligninolytic enzyme. The xylanase may be derived form various sources, for example from Chaetomium. The use of xylanase from Chainia sp culture medium is exemplified.

Gandhi, J. P. et al., *J. Chem. Tech. Biotechnol.* 60:55–60 (1994) reported studies on thermostability and pH stability of crude xylanase preparations from *Chaetomium globosum.* The optimum temperature of the xylanase was found to be in the range of 50 to 60° C., while the optimum pH was found to be pH 5.0. The enzyme was reported not to lose any of the original activity in the range of 40 to 60° C. for a period of 10 min and was reported to retain more than 70% of the original activity in the range of 70 to 100° C. for 10 min. The pH stability studies indicated that the enzyme retained all activity between pH 5 and 6 and more than 70% of the original activity over a wide range of alkaline pH values (7–10). It was suggested to use the culture filtrates for the treatment of cellulose pulps without further purification.

The xylanase of *Chaetomium cellulolyticum* and *Chaetomium trilaterale* have also been studied (Dubeau, H. et al., *Biotechnol. Lett.* 9:275–280 (1987) and Kawaminami, T. and Iitzuka, H. *J. Ferment. Technol.* 48:161–168 (1970), respectively). However, neither the thermostability nor the pH profile of the enzymes was reported. The xylanases were suggested to be of use in clarification of fruit juices. The use of these enzymes in pulp bleaching or as feed additive was not suggested.

Ganju, R. K. et al., *Can. J. Microbiol.* 35:836–842 (1989) reported the purification and characterization of two xylanases from *Chaetomium thermophile* var. *coprophile.* Two xylanases (I and II) out of several extracellular xylanases produced by *C. thermophile* var. *coprophile* were purified to homogeneity. These enzymes had molecular weights of 26.000 Daltons (xylanase I) and 7,000 Daltons (xylanase II). The temperature optima for xylanase I and II were 70 and 60° C., and they were optimally active at pH 4.8–6.4 and 5.4–6.9, respectively. The use of these xylanases in pulp bleaching or as feed additive was not suggested.

Irie et al., *Hakko Kogaku Kaishi* 70(2): 109–114 (1992) have reported the purification of a xylanase from a *Chaetomium gracile* mutant. The molecular weight was reported to be 19,000 daltons, and the xylanase contained two subunits: one having a molecular weight of 14,400 daltons and the other a molecular weight of 4,800 daltons. The pI was 8.35. The maximal xylobiose forming activity was found at pH 5.0 and 50° C. The pH range was reported to be pH 4.0–pH 7.0. Yoshino et al., *Curr. Genet.* 29:73–80 (1995) reported the isolation and sequencing of two xylanase genes from *Chaetomium gracile* wild and mutant strains and their expression in *Aspergillus nidulans.* The mature CgXA and CgXB xylanases contain 189 and 211 amino acids, respectively, and share 68.5% homology. The cgxA and cgxB genes were introduced into *Aspergillus nidulans* and reported to be expressed with their own promoters. The use of these *C. gracile* xylanases in pulp bleaching or as feed additive was not suggested.

SUMMARY OF THE INVENTION

Recognizing the importance of developing an environmentally safe and economical method of modifying plant biomass, the inventors have searched for new enzymes that would be useful in such processes.

The invention is directed to DNA sequences, including genes encoding new xylanases, the new xylanases encoded by such DNA, expression vectors containing such DNA, hosts transformed with such DNA, and any enzyme preparations from the growth of such hosts that contain the expressed xylanases, and the use of such enzyme preparations. Such uses include the enzyme-aided bleaching of wood pulp and methods of modifying plant biomass, like uses as feed additive or in baking.

BRIEF DESCRIPTION OF THE FIGURES

FIG. 2 shows the DNA (SEQ ID NO:1) and the deduced amino acid sequence (SEQ ID NO:2) of the *Chaetomium thermophilum* CBS 730.95 (ALKO4265) xlnA gene. The putative signal peptidase cleavage site is indicated by an arrow. The stop codon is indicated by an asterisk.

FIG. 3 shows the DNA (SEQ ID NO:3) and the deduced amino acid sequence (SEQ ID NO:4) of the *Chaetomium thermophilum* CBS 730.95 (ALKO4265) xlnB gene. The putative signal peptidase cleavage site is indicated by an arrow. The stop codon is indicated by an asterisk.

FIG. 4 shows the DNA (SEQ ID NO:5) and the deduced amino acid sequence (SEQ ID NO :6) of the *Chaetomium thermophilum* CBS 730.95 (ALKO4265) xlnC gene. The putative signal peptidase cleavage site is indicated by an arrow. The stop codon is indicated by an asterisk.

DETAILED DESCRIPTION OF THE PREFERRED EMBODIMENTS

Deposits

Figure 1:
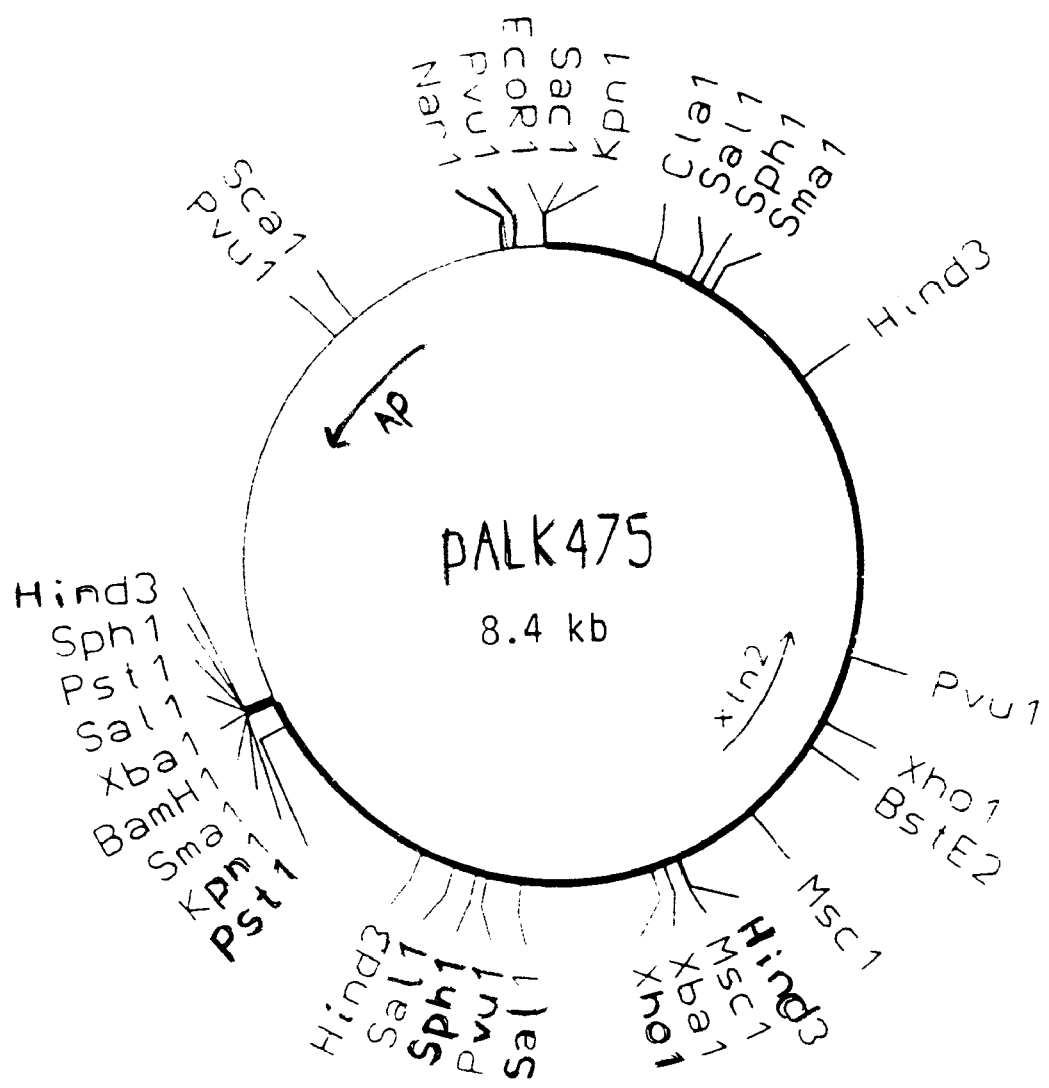
FIG. 1 shows the plasmid map of plasmid pALK475 (8.4 kb) carrying the xylanase 2 (xln2) gene of *Trichoderma reesei.*

ALKO4265. identified as *Chaetomium thermophilum* La Touche by the International Mycological Institute/Biosystem Services, was deposited on Nov. 8, 1995 at the Centralbureau Voor Schimmelcultures at Oosterstraat 1, 3742 SK BAARN, The Netherlands, and assigned CBS 730.95.

Plasmids pALK475 (containing the gene for *Trichoderma reesei* xylanase 2 (xln2)) and pALK1026, pALK1028 and pALK1049 (containing the genes for *Chaetomium thermophilum* xylanases A (xlnA), B (xlnB) and C (xlnC)) were deposited at the Deutsche Sammlung von Mikroorganismen und Zellkulturen GmbH (DSM), Mascheroder Weg 1 b, D-38124 Braunschweig, Germany on Jun. 21, 1996 and assigned accession numbers DSM 11020, DSM 11021, DSM 11022 and DSM 11023 respectively.

Definitions

In order to provide a clearer and consistent understanding of the specification and claims, including the scope to be given such terms, the following definitions are provided.

Enzyme-aided bleaching. By "enzyme-aided bleaching" is meant the extraction of lignin from cellulose pulp after the action of hemicellulose degrading enzymes with or without lignin degrading enzymes. Removal of the lignin may be restricted by hemicelluloses either physically (through reprecipitation onto the fiber surface during cooking) or chemically (through lignin-carbohydrate complexes). The hemicellulase activity partially degrades the hemicellulose, which enhances the extractability of lignins by conventional bleaching chemicals (like chlorine, chlorine dioxide, peroxide, etc.) (Viikari et al., "Bleaching with Enzymes" in Biotechnology in the Pulp and Paper Industry, Proc. 3rd Int. Conf., Stockholm, pp. 67–69 (1986); Viikari et al., "Applications of Enzymes in Bleaching" in Proc. 4th Int. Symp. Wood and Pulping Chemistry, Paris, Vol. 1, pp. 151–154 (1987); Kantelinen et al., "Hemicellulases and their Potential Role in Bleaching" in International Pulp Bleaching Conference, Tappi Proceedings, pp. 1–9 (1988)). The advantage of this improved bleachability is a lower consumption of bleaching chemicals and lower environmental loads or higher final brightness values.

Enzyme preparation. By "enzyme preparation" is meant a composition containing enzymes. Preferably, the enzymes have been extracted from (either partially or completely purified from) a microbe or the medium used to grow such microbe.

"Extracted from" means that the desired enzymes are separated from the cellular mass. This can be performed by any method that achieves this goal, including breaking cells and also simply removing the culture medium from spent cells. Therefore, the term "enzyme preparation" includes compositions containing medium previously used to culture a desired microbe(s) and any enzymes that have been released from the microbial cells into such medium during the culture, or downstream processing steps.

By a host that is "substantially incapable" of synthesizing one or more enzymes is meant a host in which the activity of one or more of the listed enzymes is depressed, deficient or absent when compared to the wild type.

Xylanase. As used herein, a xylanase is a hemicellulase that cuts the $\beta$-1,4 bonds within the xylosic chain of xylan (xylan is a polymer of D-xylose residues that are joined through $\beta$-1,4 linkages). Xylanase activity is synonymous with xylanolytic activity.

By an amino acid sequence that is an "equivalent" of a specific amino acid sequence is meant an amino acid sequence that is not identical to the specific amino acid sequence, but rather contains at least some amino acid changes (deletion, substitutions, inversions, insertions, etc.) that do not essentially affect the biological activity of the protein as compared to a similar activity of the specific amino acid sequence, when used for a desired purpose. The biological activity of a xylanase is its enzymatic activity, catalytic activity, and/or its ability to bind to hemicellulosic material. The biological activity of the XLNA, XLNB, and XLNC xylanases further includes their ability to act synergistically with other hemicellulases. Preferably, an "equivalent" amino acid sequence contains at least 80%–99% identity at the amino acid level to the specific amino acid sequence, most preferably at least 90% and in an especially highly preferable embodiment, at least 95% identity, at the amino acid level.

Thermotolerant. An enzyme is thermotolerant when it, when assayed as described in Example 5 (also higher pH and temperature values can be used), retains more than 50% of its activity when the activity value obtained by using 60 min incubation time is compared to the activity value obtained by using 5 min incubation time (in the corresponding conditions) and when the conditions are: pH $\geq 6$ and at temperature $\geq 60°$ C.

Cloning vehicle. A cloning vehicle is a plasmid or phage DNA or other DNA sequence (such as a linear DNA) that provides an appropriate nucleic acid carrier environment for the transfer of a gene of interest into a host cell. The cloning vehicles of the invention may be designed to replicate autonomously in prokaryotic and eukaryotic hosts. In fungal hosts such as Trichoderma, the cloning vehicles generally do not autonomously replicate and instead, merely provide a vehicle for the transport of the gene of interest into the Trichoderma host for subsequent insertion into the Trichoderma genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are antibiotic resistance genes. Alternatively, such markers may be provided on a cloning vehicle which is separate from that supplying the gene of interest. The word "vector" is sometimes used for "cloning vehicle."

Expression vehicle. An expression vehicle is a cloning vehicle or vector similar to a cloning vehicle but which is capable of expressing a gene of interest, after transformation into a desired host. When a fungal host is used, the gene of interest is preferably provided to a fungal host as part of a cloning or expression vehicle that integrates into the fungal chromosome, or allows the gene of interest to integrate into the host chromosome. Sequences that are part of the cloning vehicle or expression vehicle may also be integrated with the gene of interest during the integration process. In *T reesei*, sites of integration to which the gene of interest can be directed include the cbh and/or egl loci. Most preferably, the gene of interest can be directed to replace a gene that encodes an undesirable characteristic of the host.

The gene of interest is also preferably placed under the control of (i.e., operably linked to) certain control sequences such as promoter sequences provided by the vector (which integrate with the gene of interest). Alternatively, the control sequences can be those at the insertion site.

The expression control sequences of an expression vector will vary depending on whether the vector is designed to express a certain gene in a prokaryotic or in a eukaryotic host (for example, a shuttle vector may provide a gene for selection in bacterial hosts). Expression control sequences can contain transcriptional regulatory elements such as, promoters, enhancer elements, and transcriptional termination sequences, and/or translational regulatory elements, such as, for example, translational initiation and termination sites.

As described herein, ALKO4265, *Chaetomium thermophilum* La Touche, deposited as CBS 730.95, is used herein as an example of a donor of xylanase genes that are useful in several applications (e.g. in bleaching or as feed additive). Such xylanases can also be derived from other strains of the same species or from divergent organisms.

1. Cloning and Expression of the Xylanase Encoding Genes

The process for genetically engineering the hosts of the invention is facilitated through the cloning of genetic sequences that encode the desired xylanase activity and through the expression of such genetic sequences. As used herein the term "genetic sequences" is intended to refer to a nucleic acid molecule (preferably DNA). Genetic sequences that encode the desired xylanase are derived from a variety of sources. These sources include genomic DNA, cDNA, synthetic DNA and combinations thereof. Vector systems may be used to produce hosts for the production of the enzyme preparations of the invention. Such vector construction (a) may further provide a separate vector construction (b) which carries at least one desired gene to be integrated to the genome of the host and (c) a selectable marker coupled to (a) or (b). Alternatively, a separate vector may be used for the marker.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation, (2) interfere with the ability of the expression regulatory sequences to direct the expression of the mRNA, antisense RNA, or protein, or (3) interfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively.

Expression of the protein in the transformed hosts requires the use of regulatory regions functional in such hosts. A wide variety of transcriptional and translational regulatory sequences can be employed. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

In a preferred embodiment, a desired protein is secreted into the surrounding medium due to the presence of a secretion signal sequence. If a desired protein does not possess its own signal sequence, or if such signal sequence does not function well in the host, then the protein's coding sequence may be operably linked to a signal sequence homologous or heterologous to the host. The desired coding sequence may be linked to any signal sequence which will allow secretion of the protein from the host. Such signal sequences may be designed with or without specific protease sites such that the signal peptide sequence is amenable to subsequent removal. Alternatively, a host that leaks the protein into the medium may be used, for example a host with a mutation in its membrane.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3'-non-translated region may be retained for its translational termination regulatory sequence elements, or for those elements which direct polyadenylation in eukaryotic cells.

The vectors of the invention may further comprise other operably linked regulatory elements such as enhancer sequences.

In a preferred embodiment, genetically stable transformants are constructed whereby a desired protein's DNA is integrated into the host chromosome. The coding sequence for the desired protein may be from any source. Such integration may occur de novo within the cell or, in a most preferred embodiment, be assisted by transformation with a vector which functionally inserts itself into the host chromosome, for example, a vector that contains DNA elements that promote integration of DNA sequences in chromosomes.

Cells that have stably integrated the introduced DNA into their chromosomes are selected by also introducing one or more markers that allow for selection of host cells that contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transformation.

Factors of importance in selecting a particular plasmid or viral vector include: the ease with which recipient cells that contain the vector may be recognized and selected from those recipient cells that do not contain the vector; the number of copies of the vector that are desired in a particular host; and whether it is desirable to be able to "shuttle" the vector between host cells of different species.

Once the vector or DNA sequence containing the construct(s) is prepared for expression, the DNA construct (s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

Accordingly, the xylanase encoding sequences may be operably linked to any desired vector and transformed into a selected host, so as to provide for expression of such proteins in that host.

The subject matter of the invention includes also nucleic acid molecules coding for proteins having the biological activity of a xylanase and hybridizing to any of the nucleic acid molecules described above or which are defined in the following:

A nucleic acid molecule encoding a polypeptide having the enzymatic activity of a xylanase, selected from the group consisting of:

(a) nucleic acid molecules encoding a polypeptide comprising the amino acid sequence as depicted in FIG. 2, 3 or 4:
(b) nucleic acid molecules comprising the coding sequence of the nucleotide sequence as depicted in FIG. 2, 3 or 4;
(c) nucleic acid molecules encoding a polypeptide comprising the amino acid sequence encoded by the DNA insert contained in DSM 11021, DSM 11022 or DSM 11023;
(d) nucleic acid molecules comprising the coding sequence of the DNA insert contained in DSM 11021, DSM 11022 or DSM 11023;
(e) nucleic acid molecules the coding sequence of which differs from the coding sequence of a nucleic acid molecule of any one of (a) to (d) due to the degeneracy of the genetic code.
(f) nucleic acid molecules hybridizing to a molecule of any one of (a)–(d); and encoding a polypeptide having xylanase activity and having an amino acid sequence which shows at least 80% identity to a sequence as depicted in FIG. 2, 3 or 4.

The term "hybridization" in this context means hybridization under conventional hybridization conditions, preferably under stringent conditions such as described by, e.g. Sambrook et al. (1989, *Molecular Cloning, A Laboratory Manual* 2nd Edition, Cold Spring Harbor Laboratory Press, Cold Spring Harbor, N.Y.). These nucleic acid molecules that hybridize to the nucleic acid molecules according to the present invention in principle can be derived from any organism possessing such nucleic acid molecules. Preferably, they are derived from fungi, namely from those of the genera Chaetomium. Nucleic acid molecules hybridizing to the nucleic acid molecules of the present invention can be isolated, e.g., from genomic libraries or cDNA libraries of various organisms, namely fungi.

Such nucleic acid molecules can be identified and isolated by using the nucleic acid molecules of the present invention or fragments of these molecules or the reverse complements of these molecules e.g. by hybridization according to standard techniques (see Sambrook et al. (1989)).

As hybridization probe, e.g. nucleic acid molecules can be used that have exactly or substantially the same nucleotide sequence indicated in the FIGS. 2, 3 or 4 or fragments of said sequence. The fragments used as hybridization probes can also be synthetic fragments obtained by conventional synthesis techniques and the sequence of which is substantially identical to that of the nucleic acid molecules according to the invention. Once genes hybridizing to the nucleic acid molecules of the invention have been identified and isolated it is necessary to determine the sequence and to analyze the properties of the proteins coded for by said sequence.

The term "hybridizing DNA molecule" includes fragments, derivatives and allelic variants of the above-described nucleic acid molecules that code for the above-described protein or a biologically active fragment thereof. Fragments are understood to be parts of nucleic acid molecules long enough to code for the described protein or a biologically active fragment thereof. The term "derivative" means in this context that the nucleotide sequences of these molecules differ from the sequences of the above-described nucleic acid molecules in one or more positions and are highly homologous to said sequence. Homology is understood to refer to a sequence identity of at least 40%, particularly an identity of at least 60%, preferably more than 80% and still more preferably more than 90%. The deviations from the nucleic acid molecules described above can be the result of deletion, substitution, insertion, addition or combination.

Homology furthermore means that the respective nucleotide sequences or encoded proteins are functionally and/or structurally equivalent. The nucleic acid molecules that are homologous to the nucleic acid molecules described above and that are derivatives of said nucleic acid molecules are regularly variations of said molecules which represent modifications having the same biological function. They may be naturally occurring variations, such as sequences of other organisms or mutations. These mutations may occur naturally or may be achieved by specific mutagenesis. Furthermore, these variations may be synthetically produced sequences. The allelic variants may be naturally occurring variants as well as synthetically produced or genetically engineered variants.

The proteins encoded by the various variants of the nucleic acid molecules of the invention share specific common characteristics, such as enzymatic activity, molecular weight, immunological reactivity, conformation, etc., as well as physical properties, such as electrophoretic mobility, chromatographic behaviour, sedimentation coefficients, solubility, spectroscopic properties, stability, pH optimum, temperature optimum, etc. Enzymatic activity of the xylanase can be detected e.g. as described in Example 5.

The present invention furthermore relates to nucleic acid molecules the sequences of which differ from the sequences of the above-identified molecules due to degeneracy of the genetic code, and which code for a protein having the biological activity of a xylanase.

The nucleic acid molecules of the invention are preferably RNA or DNA molecules, most preferably genomic DNA or cDNA.

The xylanase encoding sequences described herein may be fused in frame to other sequences so as to construct DNA encoding a fusion protein. For example, a recombinant vector encoding a xylanase gene can be prepared as above, except that the xylanase encoding sequence is fused with a "carrier" sequence of a Trichoderma cellulase or hemicellulase, or at least one functional domain of said cellulase or hemicellulase, as described in U.S. Pat. No. 5,298.405, WO 93/24622 and in GenBank submission L25310, each incorporated herein by reference. Especially, the cellulase or hemicellulase is selected from the group consisting of CBHI, CBHII, EGI, EGII, XYLI, XYLII and MANI, or a domain thereof, such as the secretion signal or the core sequence. Mannanase has the same domain structure as that of the cellulases: a core domain, containing the active site, a hinge domain containing a serine-threonine rich region, and a tail, containing the binding domain.

Fusion peptides can be constructed that contain a mannanase or cellobiohydrolase or endoglucanase or xylanase core domain, or the core and the hinge domains from the same, fused to the xylanase sequence of the invention. The result is a protein that contains a mannanase or cellobiohydrolase or endoglucanase or xylanase core, or core and hinge regions, and a xylanase of the invention. The fusion protein contains both the mannanase or cellobiohydrolase or endoglucanase and xylanase activities of the various domains as provided in the fusion construct. The carrier polypeptide needs not have enzymatic activity or its activity may be inactivated.

Fusion proteins can also be constructed such that the mannanase or cellobiohydrolase or endoglucanase or xylanase tail or a desired fragment thereof, is included, placed before the xylanase sequence, especially so as to allow use of a nonspecific protease site in the tail as a protease site for the recovery of the xylanase from the expressed fusion protein. Alternatively, fusion proteins can be constructed that provide for a protease site in a linker that is placed before the xylanase sequence, with or without tail sequences.

Xylanase sequences or part of them can also be used as the N-terminal part of the fusion peptide, as described above, for production of other proteins. In this case, linker region can be constructed using the strategy described above.

New properties for the xylanases can be created by fusing domains, such as a cellulose binding domain (CBD), preferably with its linker, to the xylanases of the invention. Preferably, such CBD's and linkers are the corresponding CBD and linker domains of a Trichoderma cellulase or mannanase, and, most preferably, that from a *Trichoderma reesei* cellulase or mannanase.

2. The Enzyme Preparations of the Invention

Novel xylanases have been characterized from *Chaetomium thermophilum*. It has been found that strains of Chaetomium, and especially *Chaetomium thermophilum*, express and secrete xylanases that are especially useful for the pulp and paper industry. These xylanases are also useful in impure forms such as in enzyme preparations that contain, or essentially are, the spent culture medium from growth of the organism (U.S. application Ser. No. 60/008,746, incorporated herein by reference).

In a preferred embodiment, the xylanases present in the enzyme preparations of the invention and used in the methods of the invention are preferably those of Chaetomium, and especially *Chaetomium thermophilum* (CBS 730.95), and in an especially preferred embodiment, one or more of the xylanases encoded by the xylanase genes of the invention, xlnA, xlnB, and xlnC.

The invention provides methods for producing an enzyme preparation. This preparation can be partially or completely deficient in cellulolytic activity (that is, in the ability to completely degrade cellulose to glucose) and enriched in one or more xylanases desirable for pulp and paper processing. By "deficient in cellulolytic activity" is meant a reduced, lowered, or repressed capacity to degrade cellulose to glucose. Such cellulolytic activity deficient preparations, and the making of same by recombinant DNA methods, are described in U.S. Pat. No. 5,298,405, incorporated herein by reference. Spent medium from the growth of the recombinant hosts, or purified enzymes therefrom, can be used as the source of the enzyme preparations of the invention in the desired application. Further, if desired activities are present in more than one recombinant host, such preparations may be isolated from the appropriate hosts and combined prior to use in the method of the invention.

To obtain the enzyme preparations of the invention, the recombinant hosts described above having the desired properties (that is, hosts capable of expressing economically feasible quantities of the desired xylanase enzymes and optionally, those which are substantially incapable of expressing one or more cellulase enzymes) are cultivated under suitable conditions, the desired enzymes are secreted from the hosts into the culture medium, and the enzyme preparation is recovered from said culture medium by methods known in the art. The enzyme preparations of the invention can be produced by cultivating the recombinant strains in a fermentor on a suitable growth medium (such as, for example, shown in Example 5).

The enzyme preparation can be the spent culture medium with or without the transformed host cells, or can be a xylanase-containing preparation that is recovered from the same by the application of methods well known in the art. However, because the xylanase enzymes are secreted into the culture media and display activity in the ambient conditions of the hemicellulolytic liquor, it is an advantage of the invention that the enzyme preparations of the invention may be utilized directly from the culture medium with no further purification. If desired, such preparations may be filtered or lyophilized or the enzymatic activity otherwise concentrated and/or stabilized for storage. The enzyme preparations of the invention are very economical to provide and use because (1) the enzymes may be used in a crude form; isolation of a specific enzyme from the culture fluid is unnecessary and (2) because the enzymes are secreted into the culture medium, only the culture medium need be recovered to obtain the desired enzyme preparation; there is no need to extract an enzyme from the hosts. Preferably the host for such production is Trichoderma, and especially *T reesei*.

The enzyme preparations of the invention may be provided as a liquid or as a solid, for example, in a dried powder or granular or liquid form, especially nondusting granules, or a stabilized liquid, or the enzyme preparation may be otherwise concentrated or stabilized for storage or use.

The enzyme preparations of the invention can be adjusted to satisfy the requirements of specific needs in various industrial applications. It is envisioned that enzyme preparations containing one or more of the xylanases of the invention can be further enriched or made partially or completely deficient in specific enzymatic activities, so as to satisfy the requirements of a specific utility in various applications e.g. in the pulp and paper industry. A mixture of enzyme activities secreted by a host and especially a fungus, can be chosen to be advantageous in a particular industrial application, for example bleaching.

Blends may be prepared with other macromolecules that are not all secreted from the same host (for example, other enzymes such as endoglucanases, cellobiohydrolases, proteases, lipases, peroxidases, oxidases or amylases) or chemicals that may enhance the performance, stability, or buffering of the desired enzyme preparation. Non-dusting granules may be coated. Liquid enzyme preparations can be stabilized by adding a polyol such as propylene glycol, a sugar or sugar alcohol, lactic acid or boric acid, according to established methods.

If desired, an expressed protein may be further purified in accordance with conventional conditions, such as extraction, precipitation, chromatography, affinity chromatography, electrophoresis, or the like.

3. Applications

Generally, the present enzyme preparations are useful for degradation of xylan-containing substrates. In particular, the enzyme preparations of this invention are useful in the pulp and paper industry, preferably in pulp bleaching. The preparations can also preferably be used for the preparation of animal feedstuffs, in flour compositions and in dough for the preparation of breads.

Thus, in a preferred embodiment, the present invention comprises a method for enzymatically treating plant biomass under conditions of high temperature (50–80° C.) and pH 5–8 for a desired time, such as, for example, one hour.

Plant biomass is a composite material consisting primarily of a matrix of cellulose, hemicellulose, and lignin. Removal of the lignin component is desirable during the manufacture of paper pulp because of its brown color and tendency to reduce the strength of the paper product. Many processes have been developed for the removal of lignin. Typically, the wood pulp is treated with chorine-based or other toxic or environmentally harmful chemicals in order to remove the lignin component and provide for a bleached pulp. However, the undesirable by-products of this chemical treatment negatively impact upon the health and stability of the environment into which they are released. Consequently there is a great need for developing alternative, less environmentally harmful techniques to achieve pulp bleaching.

The process of the invention is preferably carried out in vitro in the hemicellulose-containing pulp. The process involves placing the enzyme preparation, spent culture medium, or concentrated mixture containing xylanase into contact with the wood pulp. Routine calculations enable those in the art to determine the optimum treatment conditions such as time, enzyme dosage, consistency of pulp, pH and temperature and other variables.

When used to treat plant pulp, the enzyme preparations of the invention may be utilized with any or all the usual bleaching chemicals, such as chlorine, chlorine dioxide, hydrogen peroxide, ozone, oxygen, sodium hydroxide, etc.

The dosage, pH, temperature, and time of enzyme treatment can all be easily varied so as to provide for maximum effectiveness of the treatment. For example, the pH may range from about pH 5 to about pH 8, the temperature may range from about 50° C. to about 80° C., the time of treatment with the enzyme preparation from about 0.5 hour to about 24 hours, and the dosage from about 20 to about 200 nkat/g pulp dry matter. Enzyme treatment can be added to various bleaching processes, that are sequences of successive chemical treatment stages. Typical bleaching processes are:

1) elemental chlorine containing sequences that can be represented by e.g. a sequence of X(C/D)EDED, where X indicates a treatment with an enzyme, such as an enzyme of the invention, C/D indicates combined treatment with elemental chlorine (C) and chlorine dioxide (D), E indicates an alkaline extraction and D indicates chlorine dioxide treatment;
2) elemental chlorine-free (ECF) sequences that can be represented by e.g. a sequence of XDEDED;
3) totally chlorine-free (TCF) sequences that can be represented by e.g. sequence of XQPPP, where Q stands for chelation, i.e. metal removal stage, and P indicates a hydrogen peroxide treatment (PPP indicates three successive peroxide stages). Typically TCF sequences also include different other stages, like different extraction stages (E, EO, EOP), ozone (Z), oxygen (O), pressurized peroxide stage (OP) etc.

The enzyme preparations of the invention satisfy the requirements of specific needs in various applications in the pulp and paper industry, including the debarking of logs and refining of wood to reduce energy demands in mechanical pulp production. In pulp beating, the enzyme preparations of the invention can be used to increase external fibrillation, and enhance or facilitate swelling of the pulp fibers, and thus improve the paper making properties of the fibers. The xylanases present in the enzyme preparation of the invention can also be used to improve pulp drainability and/or decrease water retention.

In another preferred embodiment, the enzyme preparations of the invention are used as feed additives, and thus improve animal growth rate and feed conversion. In a third preferred embodiment, the present enzyme preparation are used in baking, whereby improvement of the dough and the bread characteristics may be obtained.

The invention is described in more detail in the following examples. These examples show only a few concrete applications of the invention. It is self evident for one skilled in the art to create several similar applications. Hence the examples should not be interpreted to narrow the scope of the invention but only to clarify the use of the invention.

EXAMPLES

Example 1
Isolation of the Chromosomal DNA and Construction of the Genomic Library

*Chaetomium thermophilum* CBS 730.95 (ALKO4265) was cultivated in 2×250 ml of medium (consisting of 0.6 % Solka Floc cellulose SW 200, 0.6% distiller's spent grain, 0.3% oat spelt xylan, 0.2% $CaCO_3$, 0.15% soybean meal (defatted), 0.15% $(NH_4)_2HPO_4$, 0.1% barley bran, 0.05% $KH_2PO_4$, 0.05% $MgSO_4 \times 7\ H_2O$, 0.05% NaCl, 0.05% trace element solution-1, 0.05% trace element solution-2, 0.03% $KNO_3$), pH 6.5, in shake flasks for 3 days at 40–45° C. with shaking at 250 rpm. Trace element solution-1 contains 1.60 g of $MnSO_4$, 3.45 g of $ZnSO_4 \times 7\ H_2O$, 2.00 g of $CoCl_2 \times 6\ H_2O$ per liter. Trace element solution-2 contains 5.00 g of $FeSO_4 \times 7\ H_2O$ and 2 drops of concentrated $H_2SO_4$ per liter.

The chromosomal DNA was isolated according to Raeder and Broda, *Lett. Appl. Microbiol.* 1: 17–20 (1985). Briefly, the mycelium was washed with 20 mM EDTA and lysed in extraction buffer (200 mM TFrs-HCl (pH 8.5), 250 mM NaCl, 25 mM EDTA, 0.5% SDS). The DNA was extracted with phenol and a mixture of chloroform:isoamyl alcohol (24:1 v/v). RNA was digested with RNase.

The chromosomal DNA was partially digested with Sau3A (Boehringer Mannheim, Germany) and treated with calf intestine alkaline phosphatase. The DNA was electrophoresed on an agarose gel. DNA of about 20 kb was isolated from gel using β-agarase (Boehringer Mannheim, Germany) and used to construct the genomic Chaetomium library.

The predigested Lambda DASH® II BamHI Vector Kit (Stratagene, USA) was used to construct the library and the instructions of the manufacturer were followed in all the subsequent steps. Briefly, about 200 ng of size-fractionated DNA was ligated into 1 µg of DASH® II prepared arms, and packaged using Gigapack II packaging extract (Stratagene, USA). The titer of the library was determined by infecting *E. coli* XL1-Blue MRA (P2)-cells with serial dilutions of the packaged phage and plating on NZY plates. The library was used for screening without amplification.

Example 2
Isolation of the Genes Encoding Xylanases on the Basis of Hybridization to the *T. reesei* xln2 Gene

*E. coli* XL 1-Blue MRA (P2) -cells (Stratagene, USA) were grown in LB+0.2% maltose+10 mM $MgSO_4$, and diluted to $OD_{600}$=0.5. The cells were infected with the recombinant library for 15 min at 37° C., and plated with NZY top agar on the NZY plates. Plates were incubated at 37° C. overnight. The plaques were transferred onto a nylon filter (Hybond, Amersham, UK) according to Stratagene's instructions. The genomic library of *Chaetomium thermophilum* CBS 730.95 DNA in lambda DASH® II vector was screened with a digoxigenin-labelled 2.4 kb HindIII fragment from pALK475 containing the *T. reesei* xylanase 2 (xln2) gene (FIG. 1), according to Boehringer, DIG DNA Labeling and Detection Nonradioactive, Application Manual. Hybridization was performed at 68° C. The positive clones were picked in SM buffer/chloroform, and purified with a second round of screening.

Under these conditions 11 positive clones were found. The large scale bacteriophage lambda DNA isolation was done according to Sambrook et al., 1989. In: *Molecular Cloning: A Laboratory Manual,* 2nd ed. Cold Spring Harbor Laboratory Press, Cold Spring Harbor, N.Y. The phage DNAs were analyzed by digestion of the DNA with several restriction enzymes. Based on the hybridization analysis (using the DIG-labelled 2.4 kb *T. reesei* xln2 fragment as a probe) these phage were assigned to three classes: Eight of the analyzed phage were placed in class A (phages 1, 2, 3, 5, 6, 9, 10, 11), three in class B (phages 4, 8), and phage 7 in class C (Table 1). Phage 7 fragments gave a faint hybridization to the *T. reesei* xln2 gene.

TABLE 1

Size of the lambda clone fragments (in kb) hybridized using the 2.4 kb Trichoderma reesei xln2 gene fragment as a probe.

| lambda-clones | EcoRI fragments | SacI fragments | SalI fragments | XhoI fragments | XbaI fragments |
|---|---|---|---|---|---|
| 1 | ≧20.0 | 2.4 | 4.4 + 1.5 | 2.1 | 5.0 |
| 2 | 4.6 + 4.4 | 2.4 | 6.5 + 1.5 | 2.1 | 8.0 |
| 3 | 4.6 | 2.4 | 6.5 + 1.5 | 2.1 | 8.0 |
| 4 | 6.0 | >10.0 | 2.5 | 1.0 | 4.0 |
| 5 | 4.6 + 4.4 | 2.4 | 5.5 + 1.5 | 2.1 | 6.4 |
| 6 | 4.4 | 2.4 | 6.5 + 1.5 | 2.1 | 8.0 |
| 7 | ≧20.0 | — | >10.0 | 3.4 | 7.0 |
| 8 | 4.4 + 4.2 | 7.0 | 2.5 | 1.0 | 3.8 |
| 9 | ≧20.0 | 2.4 | 6.5 + 1.5 | 2.1 | 8.0 |
| 10 | 4.6 + 4.4 | 2.4 | 2.5 + 1.5 | 2.1 | 3.3 |
| 11 | 4.2 | 2.4 | 2.3 + 1.5 | 2.1 | 3.3 |

On the basis of the hybridization patterns the following three fragments were ligated into the pUC19 (Yanish-Perron et al., *Gene* 33. 103–119 (1985)) plasmid vector for further analysis:
1. The 4.6 kb EcoRI fragment from phage 2 (class A) was isolated and ligated into EcoRI digested and dephosphorylated pUC19 vector resulting in the plasmid pALK1026;
2. The 6.0 kb EcoRI fragment from phage 4 (class B) was isolated and ligated into EcoRI digested and dephosphorylated pUC19 vector, resulting in the plasmid pALK1028; and
3. The 7.0 kb XbaI fragment from phage 7 (class C) was isolated and ligated into XbaI digested and dephosphorylated pUC19 vector, resulting in the plasmid pALK1049.

Plasmids pALK1026, pALK1028 and pALK1049 were deposited at Deutsche Sammlung für Mikro-organismen (DSMZ) on Jun. 21, 1996 and were assigned the designation DSM11021, DSM11022 and DSM11023, respectively.

Example 3
Sequencing of the Xylanase Genes of Class A, B and C

Plasmids pALK1026, pALK1028 and pALK1049 were subjected to further restriction analysis. The sequences of the three *Chaetomium thermophilum* 730.95 xylanase genes were determined by subcloning fragments from pALK1026, pALK1028 and pALK1049 into pUC19 vector.

DNA was sequenced using the ABI (Applied Biosystems, USA) kits based on fluorescent-labelled M13 and M13rev primers, or sequence-specific primers with fluorescent-labelled dideoxynucleotides by the Taq dye primer cycle sequencing protocol in accordance with the supplier's instructions. Sequencing reactions were performed at annealing temperature of 50° C. Sequencing reactions were analyzed on ABI 373A sequencer, and the sequences obtained were characterized by using the Genetics Computer Group Sequence Analysis Software Package, version 7.2.

The DNA sequences of the xylanase genes of classes A, B and C from pALK1026, pALK1028 and pALK1049, respectively, are presented in FIGS. 2–4. Sequencing of the xylanase gene carried by the plasmid carrying the class A xylanase sequence revealed a sequence of 1281 bp (shown in FIG. 2) and an ORF (open reading frame) of 842 bp. The structural part is 783bp long and is interrupted by a single intron 59 bp in length. The polypeptide derived from the sequence is 261 amino acids in length. A putative signal peptidase processing site is found after Ala19, and the predicted mature protein has a calculated molecular weight of about 26 kDa. The sequence shows high homology towards xylanases from different organisms. At the amino acid level, the amino acid sequence encoded by this gene shows a 77.2% identity in 237 amino acids overlap with the *Chaetomium gracile* xylanase B gene, CgXB (EMBL/GenBank databases/DDBJ; accession number D49851).

Sequencing of the xylanase gene carried by the plasmid carrying the class B xylanase sequence revealed a sequence of 1174 bp (shown in FIG. 3) and an ORF of 754 bp. The structural part is 690 bp long and is interrupted by a single intron 64 bp in length. The polypeptide derived from the sequence is 230 amino acids in length. A putative signal peptidase processing site is found after Ala16, and the predicted mature protein has a calculated molecular weight of about 23 kDa. At the amino acid level, the amino acid sequence encoded by this gene shows a 70.0% identity in 227 amino acids overlap with the *Chaetomium gracile* xylanase A gene, CgXA (EMBL/GenBank databases/DDBJ; accession number D49850).

Sequencing of the xylanase gene carried by the plasmid carrying the class C xylanase sequence revealed a sequence of 1142 bp (shown in FIG. 4) and an ORF of 746 bp. The structural part is 672 bp long and is interrupted by a single intron 74 bp in length. The polypeptide derived from the sequence is 224 amino acids in length. A putative signal peptidase processing site is found after Thr18, and the predicted mature protein has a calculated molecular weight of about 23 kDa. At the amino acid level, the amino acid sequence encoded by this gene shows a 51.7% identity in 180 amino acids overlap with the *Aspergillus nidulans* xylanase gene (EMBL/GenBank databases/DDBJ; accession number Z49892).

At the amino acid level, the class A sequence has a 67.4% identity in a 190 amino acids overlap with the class B sequence, and a 42.2% identity in a 211 amino acids overlap with the class C sequence. The identity between the class B and the class C sequences is 50.6% in a 172 amino acids overlap. Thus the three xylanases of the invention are different, and are named as xlnA, xlnB and xlnC, respectively.

On the amino acid level the xylanases encoded by xlnA, xlnB and xlnC exhibit great homology to family G xylanases according to the classification of Gilkes et al., *Microbiol. Rev.* 55: 303–315 (1991).

Example 4
Production of *Chaetomium thermophilum* Xylanases A, B and C in *T. reesei*

*Trichoderma reesei* strains were constructed for *Chaetomium thermophilum* CBS 730.95 xylanase production. Strains overproduce Chaetomium xylanase in a cellulase-deficient background. Such cellulolytic activity-deficient preparations, and the making of same by recombinant DNA methods, are described in U.S. Pat. No. 5,298,405 incorporated herein by reference or Suominen et al. *Mol. Gen. Genet.* 241: 523–530 (1993)). For the overproduction of Chaetomium xylanase, xlnA, xlnB and xlnC genes were expressed from the strong *T. reesei* cbh1 promoter.

Figure 5:
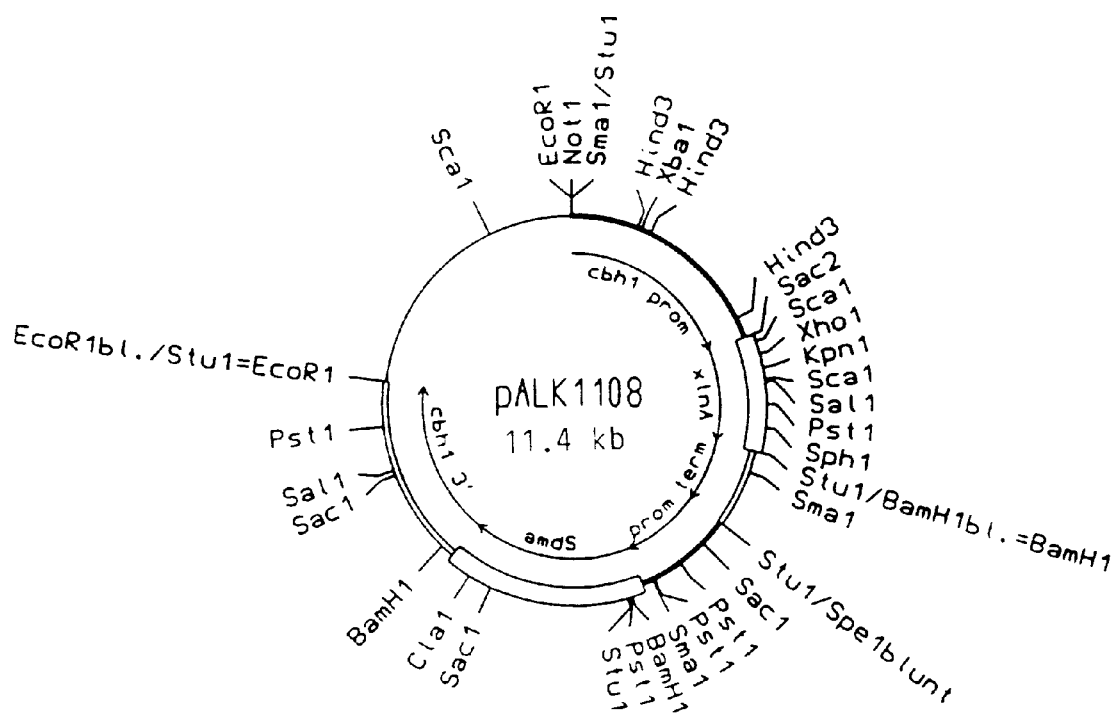
FIG. 5 shows the map of plasmid pALK1108.
Figure 6:
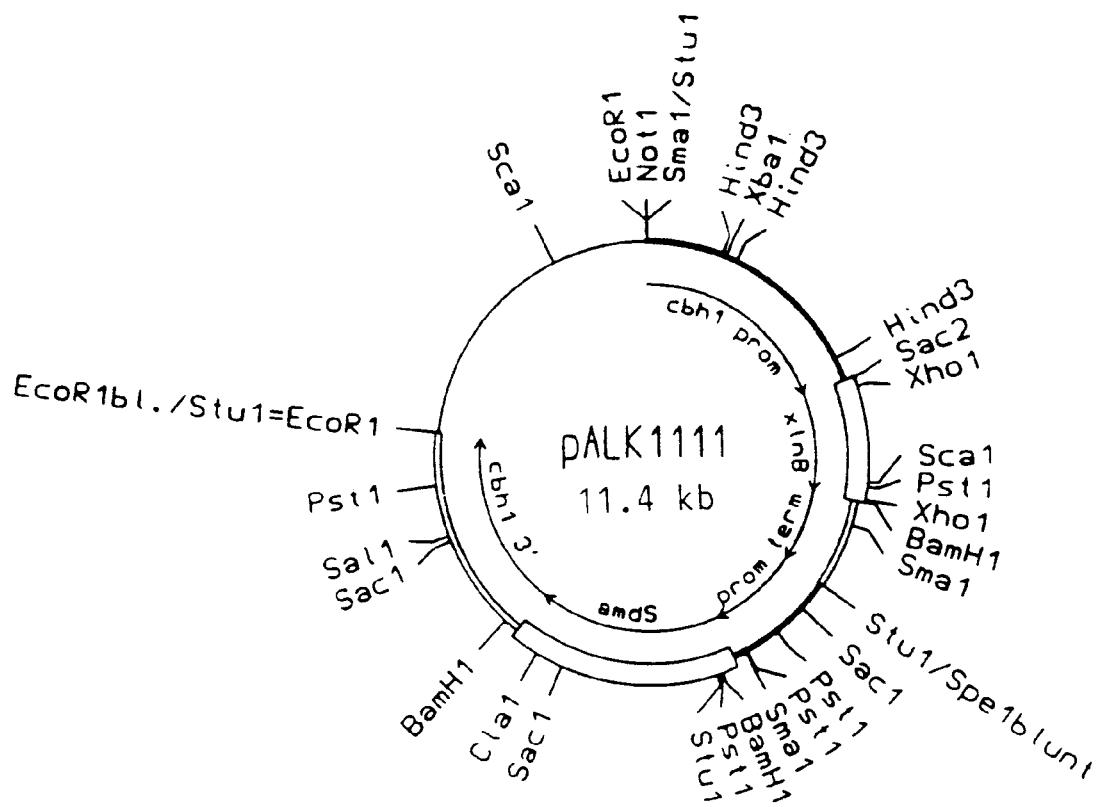
FIG. 6 shows the map of plasmid pALK1111.
Figure 7:
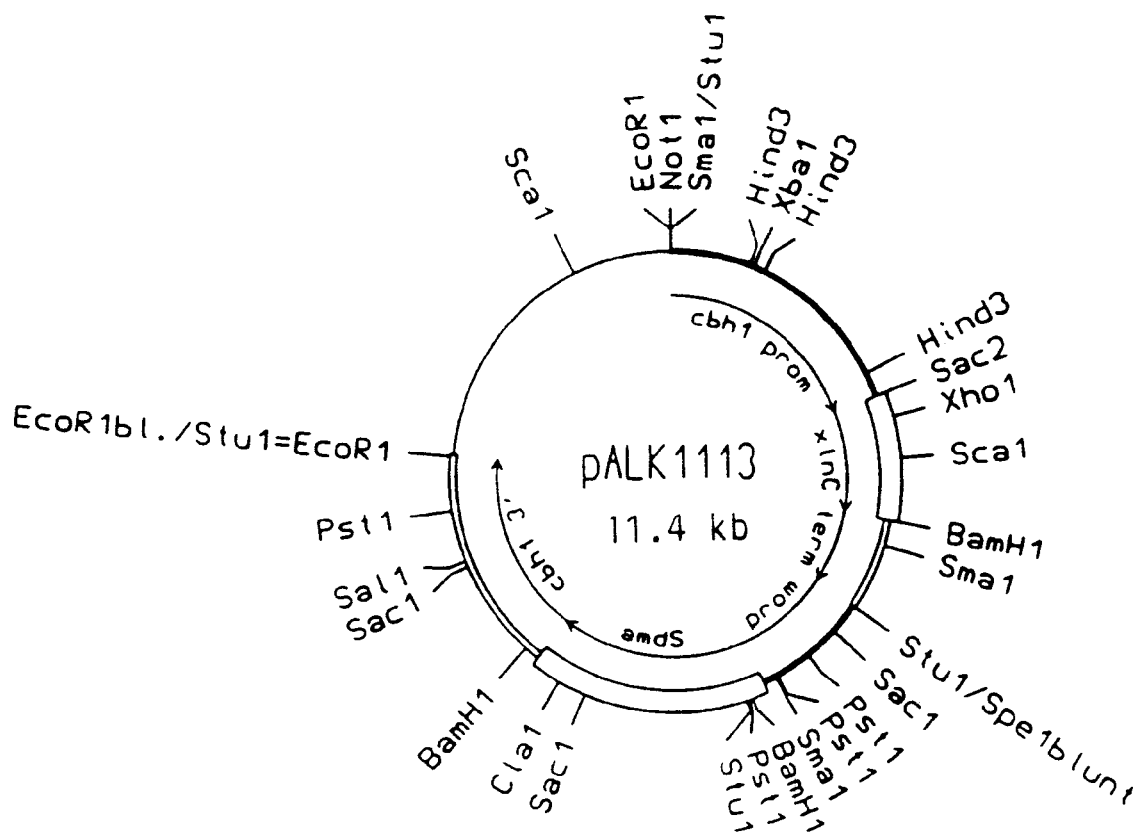
FIG. 7 shows the map of plasmid pALK1113.

The plasmids pALK1108, pALK1111 and pALK1113 (FIGS. 5–7) that were used in the construction of the Chaetomium xylanase overproducing strains, are otherwise identical to each other, except that the Chaetomium sequences differ.

The plasmids pALK1108, pALK1111 and pALK1113 contain:

cbh1 (cellobiohydrolase 1) promoter: The promoter is from *Trichoderma reesei* VTT-D-80133 (Teeri et al., *Bio/Technology* 1:696–699(1983)). The 2.2 kb EcoRI-SacII fragment (Karhunen et al., *Mol. Gen. Genet.* 241: 515–522 (1993)) is used in the constructs. The sequence preceeding the ATG was published by Shoemaker et al., *Bio/Technology* 1. 691–696 (1983)). In the *T. reesei* strain VTT-D-80133 the sequence preceeding the ATG is CCGCGGACTGCGCATC (the SacII site is underlined, an additional cytosine in the DNA sequence, compared to the sequence by Shoemaker et al., is bolded).

To make an exact fusion, the 10 nucleotides of the promoter, from the SacII site to the ATG, and the 5'-end of the xlnA or xlnB (to the internal XhoI sites, see FIGS. 5 and 6) were synthesized by using polymerase chain reaction (PCR). The exact fusion of the xlnC to the promoter was also done by PCR, in this case the whole xlnC gene was synthesized.

xlnA, xlnB and xlnC genes: The nucleotide sequences and deduced amino acid sequences of the *C. thermophilum* xylanase genes are presented in FIGS. 2–4. The genes were cloned from a genomic library of *C. thermophilum* CBS 730.95 on the basis of hybridization to the *T. reesei* xln2 gene. A 1084 bp fragment from the ATG START codon to the StuI site 239 bps after the end of the xlnA gene was used in contructing the plasmid pALK1108. A 965 bp fragment from the ATG to the XhoI site 209 bps after the end of the xlnB gene was used in the construction of plasmid pALK1111. A 977 bp fragment from the ATG to 225 bps after the end of the xlnC gene was used in the construction of the pALK1113 plasmid. The xlnA and xlnB gene fragments (from the internal XhoI site, see above) are genomic DNAs isolated from the pALK1026 and pALK1028 plasmids. The xlnC was synthesized by PCR using pALK1049 as a template.

cbh1 terminator: The 739 bp AvaII fragment (Karhunen et al., *Mol. Gen. Genet.* 241: 515–522 (1993)) starting 113 bp before the STOP of the cbh1 gene was added after the xlnA, xlnB and xlnC genes, to ensure termination of transcription.

amdS gene: The gene has been isolated from *Aspergillus nidulans* VH1-TRSX6. It codes for acetamidase (Hynes et al., *Mol. Cell. Biol.* 3: 1430–1439 (1983)). Acetamidase enables the strain to grow by using acetamide as the only nitrogen source and this characteristic has been used for selecting transformants. The 3.1 kb fragment (SpeI-XbaI) from the plasmid p3SR2 (Kelly J. and Hynes M., *EMBO J.* 4: 475–479 (1985)) was used in the plasmids. The fragment contains 1007 bps of the promoter area, 1897 bps of the coding region (introns included) and the 183 bps terminator area of the amdS gene.

cbh1 3'-fragment: The fragment was isolated from *T. reesei* ALKO2466 by using plasmid rescue (1.7 kb, BamHI-EcoRI, starting 1.4 kb after the gene's STOP, Suominen et al., *Mol. Gen. Genet.* 241: 523–530). Strain ALKO2466 derives from the strain ALKO233 (Harkki et al., *Enzyme Microb. Technol.* 13: 227–233 (1991)).

The cbh1 3'-fragment was used together with the cbh1 promoter to target the xlnA, xlnB and xlnC expression cassettes to the cbh1 locus by homologous recombination.

The expression cassettes for the *C. thermophilum* xylanase genes xlnA, xlnB and xlnC were isolated by EcoRI digestion of the pALK1108, pALK1111 and pALK1113 plasmids, respectively.

*T. reesei* ALKO4468 (EGI and EGII deficient) strain was transformed with the isolated expression cassettes: 8.8 kb EcoRI fragment of pALK1108, 8.7 kb EcoRI fragment of pALK1111 and 8.7 kb EcoRI fragment of pALK1113. Transformation was done as described by Penttilä et al., *Gene* 61: 155–164 (1987)) with the modifications described in Karhunen et al., *Mol. Gen. Genet.* 241: 515–522 (1993)). *T. reesei* transformants were transferred on a selective medium and purified through conidia.

In the host strain ALKO4468 the endoglucanase 2 (egl2) gene has been replaced by the 3.3 kb BglII-XbaI fragment from the plasmid pAN8-1 (Mattern et al., *Fungal Genet. Newlett.* 35: 25 (1988)). This fragment contains a transformation marker gene, ble from *Streptoalloteichus hindustanus* (Drocourt et al., *Nucl. Acids Res.* 18: 4009 (1990)). The ble gene confers resistance to several antibiotics, e.g. phleomycin and it is, in the construct, expressed from *Aspergillus nidulans* gpdA (glyseraldehyde-3-phosphate-dehydrogenase) promoter, *A. nidulans* trpC terminator is used to terminate the transcription. The replacement was done by using the recombinant DNA methods described in U.S. Pat. No. 5,298,405, incorporated herein by reference. In addition, the endoglucanase 1 (egl1 ) gene has been replaced by the 1.7 kb NotI-NsiI fragment from pRLM$_{ex}$30 (Mach et al., *Curr. Genet.* 25: 567–570 (1994)) containing the 0.7 kb pyruvate kinase (pki) promoter from *Aspergillus nidulans* and the 1.0 kb hygromycin B phosphotransferase (hph) gene isolated from *Escherichia coli*. The hph gene confers resistance to hygromycin.

The standard DNA methods described by Sambrook et al. (1989) In: *Molecular Cloning. A Laboratory Manual,* 2nd ed. Cold Spring Harbor Laboratory Press, Cold Spring Harbor, N.Y. were used in construction of the vectors. The restriction enzymes, T4 DNA ligase, Klenow fragment of the DNA polymerase I, T4 DNA polymerase, polynucleotide kinase and Taq polymerase were from Boehringer (Mannheim, Germany) and New England Biolabs (USA). Each enzyme was used according to the supplier's instructions. Plasmid DNA was isolated by using Qiagen columns (Qiagen GmbH. Germany) or Promega Magic Minipreps (Promega, USA) according to the manufacturer's protocols. The oligonucleotides used in the PCR-reactions and in sequencing reactions were synthetized by an ABI (Applied Biosystems, USA) 381A DNA Synthetizer. DNA sequencing was done using ABI kits based on fluorescence-labeled primers, or when sequence-specific primers are used, on fluorescence-labeled dideoxynucleotides, by the Taq cycle sequencing method according to the supplier's instructions. Sequencing reactions were analysed on an ABI 373A sequencer.

DNA fragments for cloning or transformations were isolated from agarose gels by using the Qiaex II Gel Extraction Kit (Qiagen GmbH, Germany) according to the supplier's instructions.

Example 5

Characteristics of the Chaetomium Xylanase Producing Transformants

In order to screen for production of recombinant XLNA, XLNB and XLNC, *T. reesei* transformants were cultivated in shake flasks in a medium containing 4% whey, 1.5% complex nitrogen source derived from grain, 1.5% KH$_2$PO$_4$ and 0.5% (NH$_4$)$_2$SO$_4$. Cultures were maintained at 30° C. and 250 rpm for 7 days.

The xylanase activity of transformants was determined according to Bailey et al., *J. Biotechnol.* 23: 257–270 (1992) except that the assay was performed at pH 6.5, 60° C. with an incubation time of 60 min 50 mM McIlvain's buffer. 1% (w/v) birch xylan (Roth 7500) was used as a substrate. One xylanase unit (1 nkat) is defined as the amount of enzyme that produces reducing carbohydrates having a reducing power corresponding to one nmol of xylose in one second from birch xylan under the desired assay conditions.

The CBHI phenotype of the transformants was analysed by dot blotting. The culture supernatants from shake flask cultivations were blotted onto nitrocellulose filters by a dot blot apparatus. CBHI was detected by immunostaining using a CBHI specific monoclonal antibody CI-258 (Aho et al., *Eur. J. Biochem.* 200: 643–649 (1991)) and the ProtoBlot Western blot AP system (Promega, USA) according to the recommendations of the manufacturer. CBHI deficient transformants were characterized further.

The integration and copy numbers of the transformation cassettes were verified in Southern hybridizations. In the characterized ALKO4468 transformants the cbh1 gene was replaced by the amdS marker gene and the xlnA, xlnB or xlnC construct from pALK1108, pALK1111 or pALK1113 expression cassette, respectively. The transformation host strain ALKO4468 lacks the egl2 and egl1 genes (see Example 4) and after replacement of the expression cassette into the cbh1 locus, the characterized ALKO4468 transformants do not produce Trichoderma's cellulase components EGII, EGI and CBHI.

The CBHI negative transformants with highest xylanase activities were selected for cultivations in 1 liter laboratory fermentors (Braun Biostat® M, Germany). XLNA and XLNB producing transformants were cultivated in laboratory fermentors at pH 4.4±0.4, XLNC producing transformants at pH 5.2±0.4.

The xylanase activities were determined according to Bailey et al., *J. Biotechnol.* 23: 257–270 (1992) except that the assays were performed either at pH 5.3, 50° C., 5 min in 50 mM sodium citrate buffer or at pH 6, 60° C. or pH 7, 70° C. with an incubation time of 5 min or 60 min in 50 mM McIlvain's buffer. 1% (w/v) birch xylan (Roth 7500) was used as a substrate. The transformants with the highest xylanase XLNA, XLNB and XLNC production are shown in Table 2.

The xylanase activity of the host strain *T. reesei* ALKO4468 at pH 7, 70° C., 60 min was artificially set from nkats to value 1. The other values are relative activities compared to this artificial value.

The highest xylanase activity of the *T. reesei* host strain was obtained at pH 5.3, 50° C. Under these conditions the xylanase activities of the *C. thermophilum* CBS730.95 xylanases XLNA, XLNB or XLNC producing transformants were 4–7 times higher (590, 489 and 351 XU) than that of the host strain ALKO4468 (86 XU).

Considerably higher xylanase activities for XLNA and XLNB were obtained when the activity was measured at pH 6, 60° C., 5 min (820 and 755 XU) or at pH 7, 70° C., 5 min (1 188 and 841 XU). At pH 7, 70° C., 5 min the activities were 84 and 120 fold higher than that of the ALKO4468 host strain; compared to the xlnA and xlnB gene donor strain ALKO4265, the activities were 100 and 150 fold higher.

XLNA and XLNB seem to be thermotolerant. XLNA retained 88% (721 XU) of its activity at pH 6, 60° C. and 62% (740 XU) of its activity at pH 7, 70° C. when the incubation time was increased from 5 to 60 minutes. Under the same conditions XLNB retained 65% (491 XU) and 17% (143 XU) of its activity.

XLNC differed from XLNA and XLNB. It had higher activity at pH 5.3, 50° C., 5 min, compared to pH 7, 70° C. 5 min.

Table 2. The relative xylanase activities of *T. reesei* transformants ALKO4468/xlnA (ALKO4468/1108/7), ALKO4468/xlnB (ALKO4468/1111/44) and ALKO4468/ xlnC (ALKO4468/1113/34) producing *C. thermophilum* CBS730.95 xylanases XLNA, XLNB and XLNC respectively. ALKO4468 is the *T. reesei* host strain and ALKO4265 is the gene donor, *C. thermophilum* CBS730.95. The xylanase activity of the host strain *T. reesei* ALKO4468 at pH 7, 70° C., 60 min was artificially set to value 1. The other values are relative activities compared to this artificial value.

| Strain | XU/ml pH 5.3, 50° C., 5 min | XU/ml pH 6, 60° C., 5 min | XU/ml pH 6, 60° C., 60 min | XU/ml pH 7, 70° C., 5 min | XU/ml pH 7, 70° C., 60 min |
|---|---|---|---|---|---|
| ALKO4468/ xlnA | 590 | 820 | 721 | 1188 | 740 |
| ALKO4468/ xlnB | 489 | 755 | 491 | 841 | 143 |
| ALKO4468/ xlnC | 351 | nd | nd | 65 | nd |
| ALKO4468 | 86 | nd | nd | 10 | 1 |
| ALKO4265 | nd | nd | nd | 8 | 4 |

XU = relative xylanase units
nd = not determined

Figure 8A:
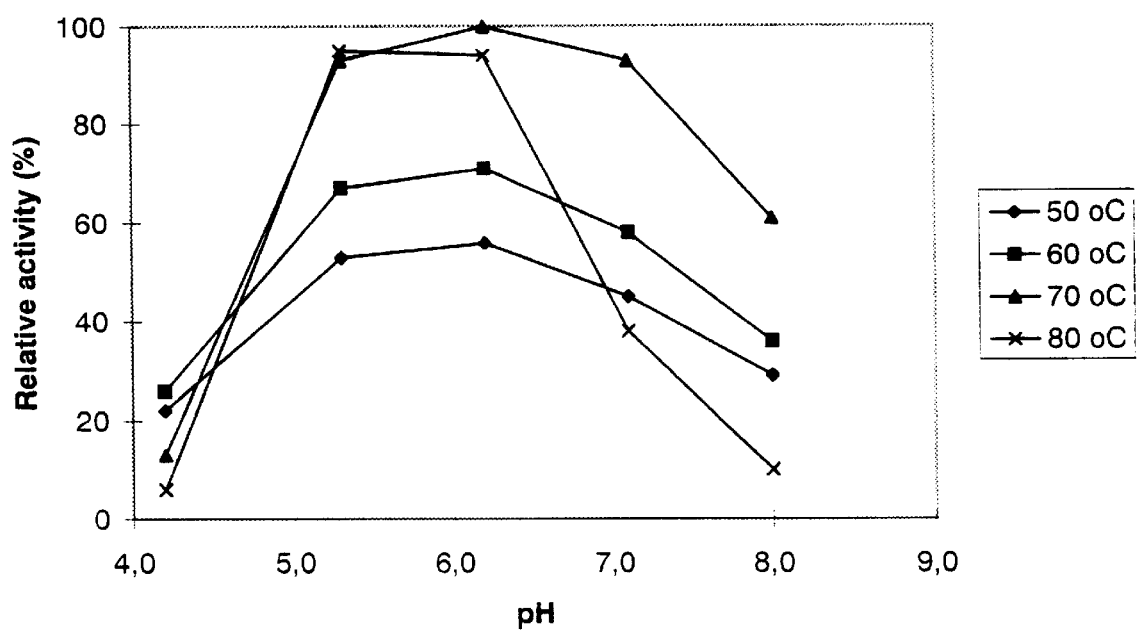
FIG. 8 (A, B and C) show the pH dependencies of the xylanase activities of *T. reesei* transformants producing *C. thermophilum* CBS 730.95 xylanase A (FIG. 8A), xylanase B (FIG. 8B) and xylanase C (FIG. 8C). Enzyme activity was measured after 5 min incubation.
Figure 8B:
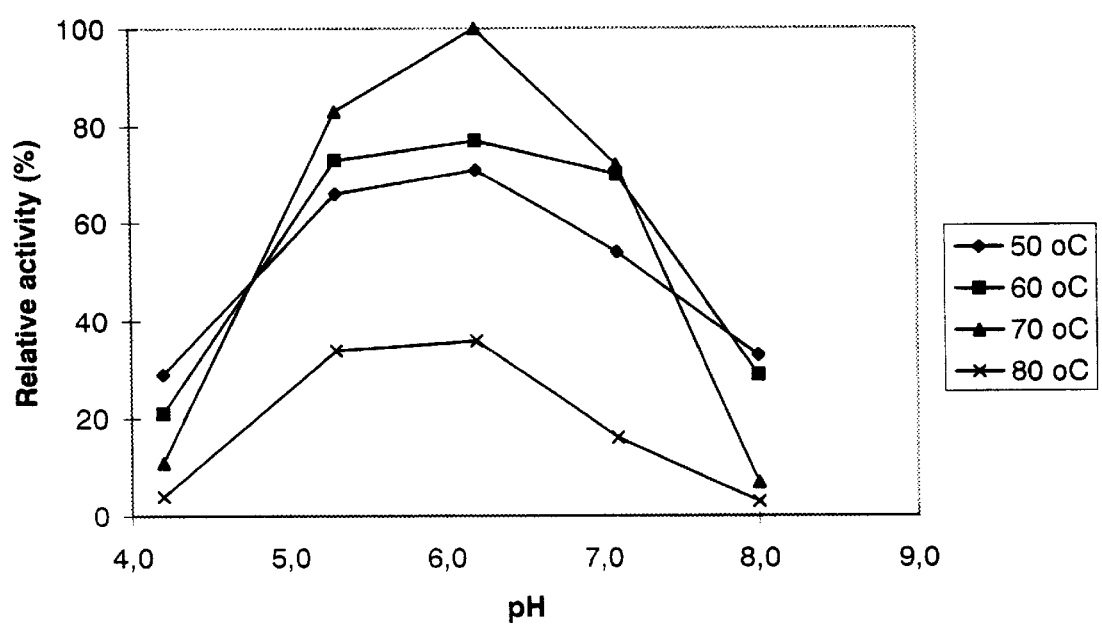
Figure 8C:
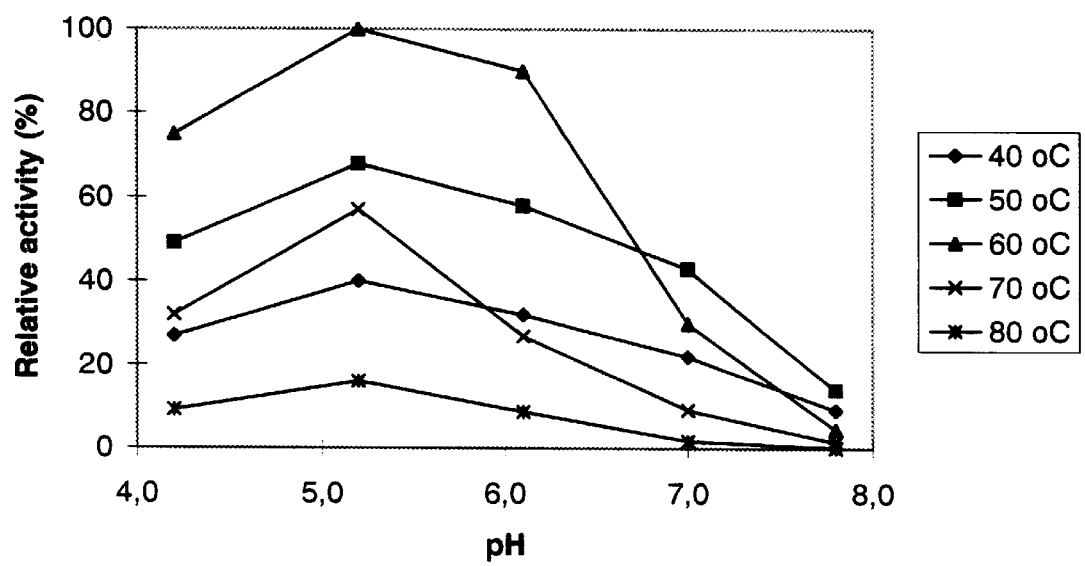
Figure 9A:
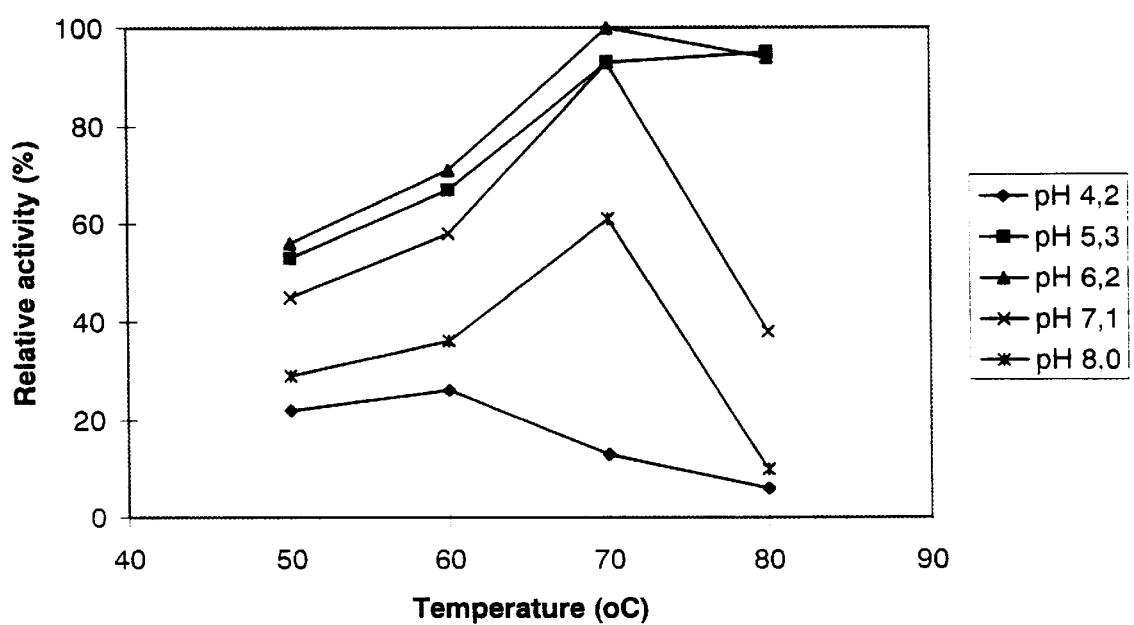
FIG. 9 (A, B and C) show the temperature dependencies of the xylanase activities of *T. reesei* transformants producing *C. thermophilum* CBS 730.95 xylanase A (FIG. 9A) and xylanase B (FIG. 9B) and xylanase C (FIG. 9C). Enzyme activity was measured after 5 min incubation.
Figure 9B:
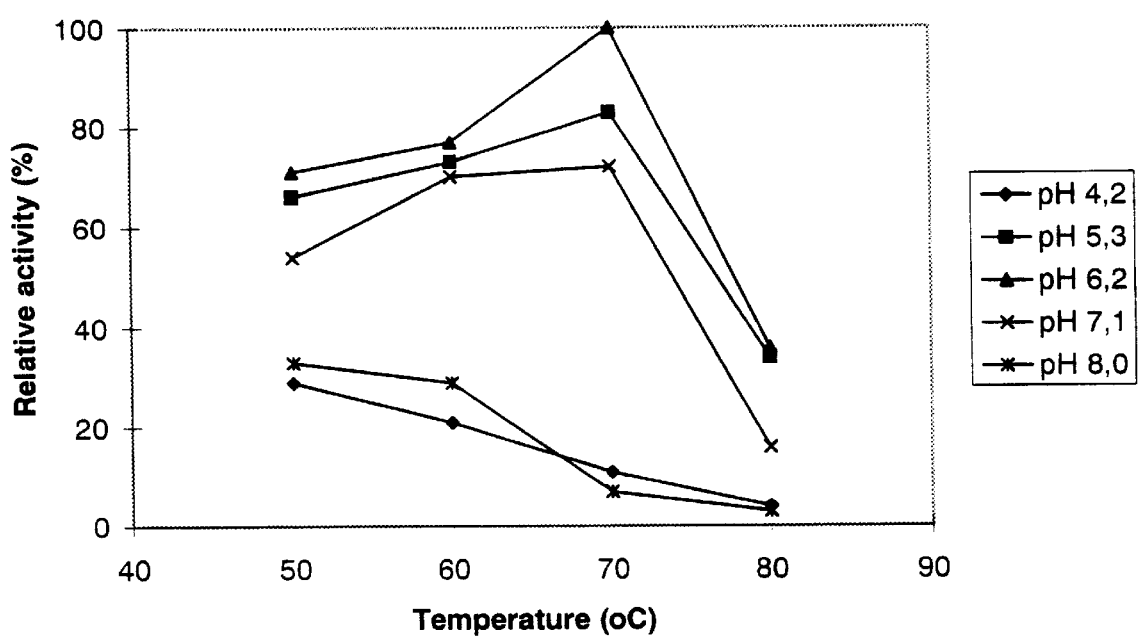
Figure 9C:
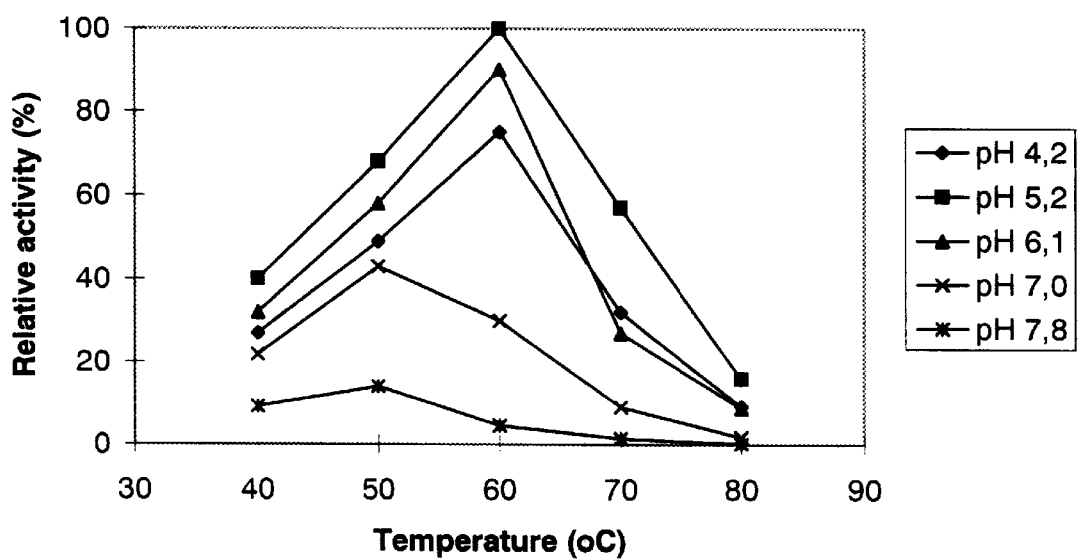

The pH and thermal dependencies of the *C. thermophilum* CBS730.95 XLNA, XLNB and XLNC produced by *T. reesei* were determined. Samples from the culture supernatants were diluted in 50 mM McIlvain's buffer of corresponding pH in a range of pH 4.2–8.0. The thermal dependencies were measured in a range of 40–80° C. The activities were determined after 5 min incubation. The pH profiles are shown in FIG. 8 and temperature profiles in FIG. 9.

Recombinant XLNA was more thermophilic than XLNB. At about pH 5–6 XLNA showed maximum activity at 70–80° C.; at about pH 7 the maximum activity was observed at 70° C.; considerable activity was observed at pH 8, 70° C. Recombinant XLNB exhibited maximum activity at about pH 5–7, 50–70° C. Neither XLNA nor XLNB showed remarkable xylanase activity at pH 4.

Thus, as evidenced by the above data, the present enzymes can be used in particular in the neutral pH region and even at moderately alkaline pH-values. This feature makes the enzymes highly useful in modern ECF and TCF bleaching sequences. In particular, enzyme treatments with the present xylanases can be combined with alkaline extraction/washing steps (E, E$_p$, E$_O$) and peroxide (P) treatment steps. Said feature is also quite unexpected, because the known fungal xylanases are generally active at lower pH.

XLNC was less thermophilic than XLNA and XLNB. XLNC had its optimum at 60° C., at pH 4–6.

Figure 10:
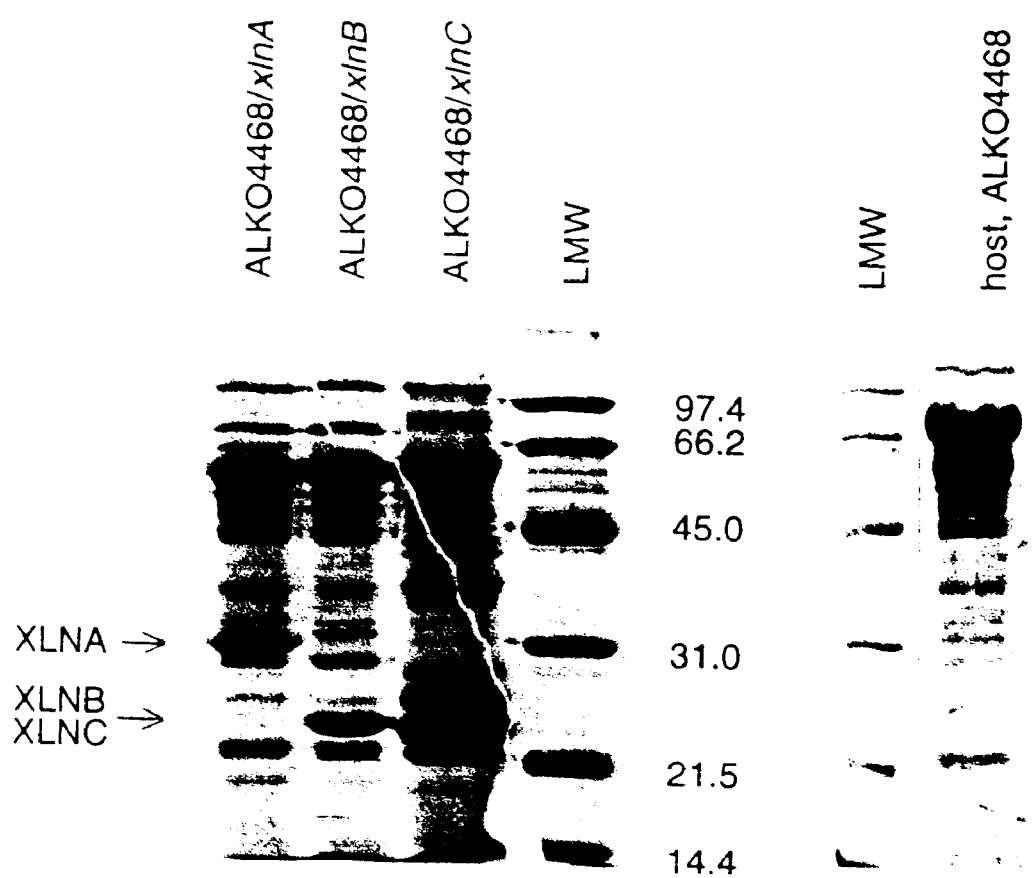
FIG. 10 shows SDS-PAGE analysis of the culture filtrates of the *T. reesei* transformants producing *C. thermophilum* CBS 730.95 xylanases XLNA, XLNB and XLNC. *T. reesei* host strain ALKO4468 and the recombinant strains ALKO4468/xlnA (ALKO4468/1108/7) and ALKO4468/xlnB (ALKO4468/1111/44) were cultivated in a laboratory fermentor. The XLNC production strain ALKO4468/xlnC (ALKO4468/1 113/34) was grown in a shake flask. The masses of the molecular weight markers (in kDa) are shown on the right. The positions of XLNA, XLNB and XLNC are indicated.

The expression of the *C. thermophilum* CBS730.95 xylanases XLNA, XLNB and XLNC produced by *T. reesei* ALKO4468 were verified by SDS polyacrylamide gel electrophoresis (PAGE) analysis (FIG. 10). Samples containing 30 μg of total secreted protein were run in 12% gel and visualized with Coomassie brilliant blue staining. All three *C. thermophilum* CBS730.95 xylanases were expressed in considerable amounts in *T. reesei* ALKO4468.

Example 6

Fusion Proteins

A recombinant vector encoding a xylanase gene is prepared by fusing the xylanase encoding sequence with the sequence of a Trichoderma cellulase or hemicellulase or at least one functional domain of said cellulase or hemicellulase, as described in U.S. Pat. No. 5,298,405, WO 93/24621 and in GenBank submission L25310, incorporated herein by reference. Especially, the enzyme is selected from the group consisting of CBHI, CBHII, EGI EGII, XYLI, XYLII and MANI, or a domain thereof, such as the secretion signal or the core sequence.

Fusion proteins can be constructed that contain an N-terminal mannanase or cellobiohydrolase or endoglucanase core domain or the core and the hinge domains from the same, fused to the Chaetomium xylanase sequence. The result is a protein that contains N-terminal mannanase or cellobiohydrolase or endoglucanase core or core and hinge regions, and a C-terminal Chaetomium xylanase. The fusion protein contains both the mannanase or cellobiohydrolase or endoglucanase and xylanase activities of the various domains as provided in the fusion construct. The carrier polypeptide needs not have enzymatic activity or its activity may be inactivated.

Fusion proteins can also be constructed such that the mannanase or cellobiohydrolase or endoglucanase tail or a desired fragment thereof, is included, placed before the Chaetomium xylanase sequence, especially so as to allow use of a nonspecific protease site in the tail as a protease site for the recovery of the xylanase sequence from the expressed fusion protein. Alternatively, fusion proteins can be constructed that provide for a protease site in a linker that is placed before the Chaetomium xylanase, with or without tail sequences.

Chaetomium xylanases can also be used as the N-terminal part of the fusion protein, as described above, for production of any wanted protein. In this case, linker region can be constructed using the strategy described above.

New properties for the xylanases can be created by fusing domains, such as a cellulose binding domain (CBD), preferably with its linker, to the xylanases of the invention. Preferably, such CBD's and linkers are the corresponding CBD and linker domains of a Trichoderma cellulase or mannanase, and, most preferably, that from a *Trichoderma reesei* cellulase or mannanase.

Example 7

Hosts

The recombinant construct encoding the desired proteins or fusion proteins are prepared as above, and transformed into a filamentous fungi such as Aspergillus spp., or Trichoderma spp., preferably *T. reesei*.

Example 8

TCF Bleaching of Softwood Pulp using *Chaetomium thermophilum* CBS 730.95 Xylanases XLNA and XLNB Secreted from Trichoderma A bleaching experiment was carried out to determine the usefulness of xylanases XLNA and XLNB of *Chaetomium thermophilum* CBS 730.95 secreted from Trichoderma in a TCF (totally chlorine free) bleaching of kraft pulp.

Spent media from cultures of the Trichoderma host secreting XLNA or XLNB xylanases (Example 5) were added to Scandinavian oxygen-delignified softwood kraft pulp (kappa number 20, brightness 34%) in the amount of 100 nkat/g of pulp dry matter. Xylanase activity expressed as nkat was measured according to Bailey et al., J. Biotechnol. 23:257–270 (1992) by using Roth (no. 7500) birch xylan as substrate at 70° C., pH 7.0 with a 5 minutes incubation time. The enzyme treatments were done at pH 7 and 70° C. for one hour. Reference pulp was treated in the same way but without enzyme addition. Bleaching was performed with QP sequence to test the response of enzyme treatment in peroxide based bleaching (Q indicates chelation stage and P peroxide stage). The bleaching sequences can also typically include more than one peroxide (P) stage, as well as different extraction stages (like E, EO, EOP, ozone stages (Z), pressurized peroxide stages (OP), etc.; E indicates an alkaline extraction, O oxygen). The chelation stage (Q) and the hydrogen peroxide stage (P) were carried out under the conditions mentioned in Table 3. Bleaching chemicals in the P stage were the following: 3% $H_2O_2$, 3% NaOH, 0.2% diethylenetriaminepentaacetic acid (DTPA) and 0.5% $MgSO_4$. The results of the bleaching experiment are shown in Table 3.

TABLE 3

|  | Reference | XLNA | XLNB |
|---|---|---|---|
| Enzyme treatment |  |  |  |
| Consistency, % | 3.5 | 3.5 | 3.5 |
| Retention time, hours | 1 | 1 | 1 |
| Enzyme dosage, nkat/g | 0 | 100 | 100 |
| Temperature, ° C. | 70 | 70 | 70 |
| pH, start / end | 7.2/7.2 | 7.2/7.2 | 7.3/7.3 |
| Q-stage |  |  |  |
| Consistency, % | 3 | 3 | 3 |
| Retention time, hours | 1 | 1 | 1 |
| Temperature at the end, ° C. | 64 | 64 | 64 |
| pH at the end | 5.0 | 5.5 | 5.5 |
| EDTA, % of dry matter | 0.2 | 0.2 | 0.2 |
| P-stage |  |  |  |
| Consistency, % | 10 | 10 | 10 |
| Retention time, hours | 3 | 3 | 3 |
| Temperature, ° C. | 80 | 80 | 80 |
| pH, start / end | 11.4/10.8 | 11.4/10.8 | 11.4/10.8 |
| Peroxide dosage, % | 3 | 3 | 3 |
| Peroxide consumed, % | 2.3 | 2.3 | 2.2 |
| Brightness, % | 63.3 | 64.3 | 63.8 |
| Viscosity, ml/g | 990 | 990 | 980 |

As can be seen in Table 3, after the pretreatment with Trichoderma spent culture media containing *Chaetomium thermophilum* CBS 730.95 xylanases XLNA and XLNB final pulps had 1.0 to 0.5 units higher brightness values than reference. Conditions in the enzyme pretreatment were not optimal for XLNB (see Table 2), and thus lower brightness value was obtained, compared to XLNA. Under the used conditions *T. reesei* xylanases are not active (Table 2) and have no effect on the brightness obtained.

The amount of peroxide consumed was not increased. Enzyme treatments did not affect the viscosity of the pulps because of low cellulase degrading activity.

Example 9

TCF Bleaching of Hardwood Pulp Using *Chaetomium thermophilum* CBS 730.95 Xylanases XLNA and XLNB Secreted from Trichoderma as well as Xylanase Activity Containing Spent Culture Medium of *C. thermophilum* CBS 730.95

A bleaching experiment was carried out to determine the usefulness of xylanases XLNA and XLNB of *Chaetomium thermophilum* CBS 730.95 secreted from Trichoderma and the xylanase activities of the spent culture medium of *Chaetomium thermophilum* CBS 730.95 in a TCF bleaching of hardwood kraft pulp.

Spent media from cultures of the Trichoderma host secreting XLNA and XLNB xylanases (Example 5) as well as of

*C. thermophilum* CBS 730.95 were added to Scandinavian millwashed hardwood kraft pulp (kappa number 8.9) in the amount of 100 nkat/g of pulp dry matter. Xylanase activity expressed as nkat was measured according to Bailey et al., J. Biotechnol. 23:257–270 (1992) by using Roth (no. 7500) birch wood xylan as substrate at 70°, pH 7.0 with a 5 minutes incubation time. The enzyme treatments were done at pH 7 and 70° C. for one hour. Reference pulp was treated in the same way but without enzyme addition. Bleaching was performed with QP sequence. The chelation stage (Q) and the hydrogen peroxide stage (P) were carried out under the conditions mentioned in Table 4. Bleaching chemicals in the P stage were the following: 3% $H_2O_2$, 3% NaOH, 0.2% diethylenetriaminepentaacetic acid (DTPA) and 0.5% $MgSO_4$. The results of the bleaching experiment are shown in Table 4.

TABLE 4

|  | Reference | XLNA | XLNB | CBS 730.95 |
|---|---|---|---|---|
| Enzyme treatment |  |  |  |  |
| Consistency, % | 3.5 | 3.5 | 3.5 | 3.5 |
| Retention time, hours | 1 | 1 | 1 | 1 |
| Enzyme dosage, nkat/g | 0 | 100 | 100 | 100 |
| Temperature, ° C. | 70 | 70 | 70 | 70 |
| pH, start / end | 6.8/7.0 | 6.8/7.0 | 6.9/7.0 | 6.9/6.9 |
| Q-stage |  |  |  |  |
| Consistency, % | 3 | 3 | 3 | 3 |
| Retention time, hours | 1 | 1 | 1 | 1 |
| Temperature at the end, ° C. | 66 | 66 | 66 | 66 |
| pH at the end | 5.5 | 5.5 | 5.5 | 5.5 |
| EDTA, % of dry matter | 0.2 | 0.2 | 0.2 | 0.2 |
| P-stage |  |  |  |  |
| Consistency, % | 10 | 10 | 10 | 10 |
| Retention time, hours | 3 | 3 | 3 | 3 |
| Temperature, ° C. | 80 | 80 | 80 | 80 |
| pH, start / end | 11.3/11.1 | 11.3/11.1 | 11.3/11.1 | 11.3/11.1 |
| Peroxide dosage, % | 3 | 3 | 3 | 3 |
| Peroxide consumed, % | 2.7 | 2.7 | 2.7 | 2.8 |
| Brightness, % | 78.9 | 80.3 | 79.4 | 79.2 |
| Viscosity, ml/g | 700 | 720 | 725 | 705 |

Higher brightness values was obtained when *Chaetomium thermophilum* CBS 730.95 xylanases XLNA and XLNB, secreted from the recombinant *T. reesei* strains, were used values, compared to the spent culture medium of *Chaetomium thermophilum* CBS 730.95. As can be seen in Table 4, after the pretreatment with Trichoderma spent culture media containing XLNA and XLNB final pulps had 1.4 to 0.5 units higher brightness values than reference. The spent culture medium of *C. thermophilum* CBS 730.95 containing several xylanase activities had only a minor effect on the brightness with the used amount of xylanase activity (0.3 units). The amount of peroxide consumed was not increased. Enzyme treatments with XLNA and XLNB did not affect the viscosity of the pulps because of the low cellulase degrading activity.

XLNA and XLNB xylanases produced separately in *T. reesei* host strain gave higher brightness than *C. thermophilum* CBS 730.95 culture medium. *C. thermophilum* CBS 730.95 culture medium contains several xylanases that all seem not to be as effective in the application.

Example 10

Bleaching Experiment Using *Chaetomium thermophilum* Xylanases Secreted from Trichoderma and Chlorine Chemicals A bleaching experiment can be carried out to determine the usefulness of *Chaetomium thermophilum* CBS 730.95 xylanases secreted from Trichoderma in elementary chlorine free (ECF) or chlorine containing bleaching of pulp.

Spent media from cultures of the Trichoderma host secreting *Chaetomium thermophilum* CBS 730.95 xylanases are added to softwood or hardwood pulp in the amount of 20–200 nkat/g of pulp dry matter. The enzyme treatments are performed at pH 5–8 and at 50–80° C. for one to three hours. Reference pulp is kept under the same conditions without enzyme addition. After the enzyme treatments bleaching is performed for example with C/DEDED or DEDED sequence, where C stands for elemental chlorine, D stands for a chlorine dioxide treatment and E stands for alkaline extraction.

Having now fully described the invention, it will be understood by those with skill in the art that the invention may be performed within a wide and equivalent range of conditions, parameters and the like, without affecting the spirit or scope of the invention or any embodiment thereof. All references cited herein are fully incorporated herein by reference.

What is claimed is:

1. A purified polypeptide having xylanase activity which is xylanase A from *Chaetomium thermophilum* comprising SEQ ID No: 2 or amino acids 20–261 of SEQ ID No: 2.

2. A purified polypeptide having xylanase activity which is xylanase B from *Chaetomium thermophilum* comprising SEQ ID No: 4 or amino acids 17–230 of SEQ ID No: 4.

3. A purified polypeptide having xylanase activity which is xylanase C from *Chaetomium thermophilum* comprising SEQ ID No: 6 or amino acids 19–224 of SEQ ID No: 6.

4. An enzyme preparation comprising the polypeptide of any one of claims 1–3 which is liquid.

5. An enzyme preparation comprising the polypeptide of any one of claims 1–3 which is dry.

6. A method for treating wood-derived pulp or fiber comprising the step of adding a polypeptide of any one of claims 1–3 or an enzyme preparation according to claims 4 or 5 to wood-derived mechanical or chemical pulp or secondary fiber.

7. A method of bleaching pulp comprising the step of contacting said pulp with a polypeptide of any one of claims 1–3 or an enzyme preparation according to claims 4 or 5.

8. A method of improving the quality of animal feed which comprises treating animal feed comprising plant material with a polypeptide of any one of claims 1–3 or an enzyme preparation according to claims 4 or 5.

9. A method for baking which comprises adding a polypeptide of any one of claims 1–3 or an enzyme preparation according to claims 4 or 5 to flour used to prepare dough.

10. A method of degrading xylan-containing substrate comprising contacting said substrate with a polypeptide of any one of claims 1–3 or an enzyme preparation according to claims 4 or 5 under appropriate conditions for a time effective for said degradation to occur.

11. A method for preparing animal feed comprising mixing a polypeptide of any one of claims 1–3 or an enzyme preparation according to claims 4 or 5 with animal feed.

12. An animal feed composition comprising a polypeptide of any one of claims 1–3 or an enzyme preparation according to claims 4 or 5.

13. The method of claim 9 wherein the dough is to prepare bread.

14. A flour composition comprising a polypeptide of any one of claims 1–3 or an enzyme preparation according to claim 4 or 5.

15. A dough composition comprising a polypeptide of any one of claims 1–3 or an enzyme preparation according to claims 4 or 5 as a bread improving component.

16. A method for producing wood pulp comprising contacting wood under conditions for a sufficient time to effect production of wood pulp with a polypeptide of any one of claims 1–3 or an enzyme preparation according to claims 4 or 5.

* * * * *

UNITED STATES PATENT AND TRADEMARK OFFICE
CERTIFICATE OF CORRECTION

PATENT NO.   : 6,228,629 B1
DATED        : May 8, 2001
INVENTOR(S)  : Paloheimo et al.

It is certified that error appears in the above-identified patent and that said Letters Patent is hereby corrected as shown below:

<u>Title page,</u>
Item [73], Assignee, please delete "Röhn" and insert therein -- Röhm --.
Item [60], Related U.S. Publication Data, please delete "60/020,389" and insert therein -- 60/020,839 --.

Signed and Sealed this

Second Day of December, 2003

JAMES E. ROGAN
*Director of the United States Patent and Trademark Office*

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 1281 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Chaetomium thermophilum
      (B) STRAIN: CBS730.95

(ix) FEATURE:
    (A) NAME/KEY: exon
    (B) LOCATION:195..423
    (D) OTHER INFORMATION:/product= "XLNA"

(ix) FEATURE:
    (A) NAME/KEY: exon
    (B) LOCATION:483..1039
    (D) OTHER INFORMATION:/product= "XLNA"

(xi) SEQUENCE DESCRIPTION: SEQ ID NO: 1:

| | | | | | |
|---|---|---|---|---|---|
| ACTGTCTAGA | TGCAACTATA | CCCAGCAGAG | GTTGTGATCG | AGCTCAAGTC | TAAACTTGGA | 60 |
| AGAAGCACCC | AGAGGACAGG | TTTGGAGGAC | CTCTCACGAA | TACATAAAGG | CCTCAAGACC | 120 |
| TCTCCCAGAG | CTTCCTCTAC | TCCTTTCATC | TTCACCGACC | GTGATACAAA | CAGAAAATAG | 180 |
| CATCATATAT | CAAGATGGTC | AACTTCTCAA | CTCTCTTCCT | CGCGGCTTCG | ACCGCAGCAC | 240 |
| TTGCTGCTGC | TGCCCCCAGC | ATCGAGAAGC | GTCAGACGCT | CACCAGCAGT | GCCACCGGCA | 300 |
| CCCACAATGG | CTACTACTAC | AGCTTCTGGA | CCGATGGCCA | AGGCAACATT | CGCTTCAACC | 360 |
| TCGAGAGCGG | TGGCCAGTAC | AGCGTGACAT | GGTCTGGTAA | CGGCAACTGG | GTTGGCGGCA | 420 |
| AAGGTATGTC | TCTTTAATGT | TTCCAGCGCT | ATGGAATGAA | CTAAATGCTA | ACCTGTTAAC | 480 |
| AGGCTGGAAC | CCCGGTACCG | ATAACCGTGT | CATCAACTAC | ACAGCCGACT | ACAGACCCAA | 540 |
| CGGCAACTCC | TACCTCGCCG | TCTACGGCTG | GACCCGCAAC | CCGCTGATCG | AGTACTACGT | 600 |
| GGTCGAGAGC | TTCGGCACTT | ACGACCCGTC | GACGGGCGCC | ACCCGCATGG | GCAGCGTGAC | 660 |
| CACCGACGGC | GGCACCTACA | ACATCTACCG | CACGCAGCGC | GTCAACGCGC | CCTCCATCGA | 720 |
| GGGCACCAAG | ACCTTCTACC | AATACTGGTC | TGTGCGCACC | TCCAAGCGCA | CCGGCGGTAC | 780 |
| TGTTACCATG | GCCAACCACT | TCAATGCTTG | GAGGCAGGCT | GGTCTGCAGC | TGGGTTCCCA | 840 |
| TGATTATCAG | ATTGTGGCTA | CTGAGGGTTA | CTACTCGTCT | GGCTCGGCGA | CTGTCAATGT | 900 |
| TGGCGGCAGC | ACTACTGGTG | GTAACAATGG | CGGTAACAAT | GGCGGTAACA | ATGGCGGTAA | 960 |
| CAATGGCGGC | AACACTGGCT | CGAACGTGAG | TATCTCCAGA | CCCCGCAAGA | TGGGAAGTTT | 1020 |
| AGCCAGTACA | AGAAGCTAAC | AAGCATGCAG | TGCTCTCCTA | TTTGGGGTCA | GTGCGGCGGC | 1080 |
| CAGGGCTGGA | CCGGCCCGAC | CTGCTGCCAG | AGCGGCTCGA | CCTGCCGCTT | CCAGAACAAC | 1140 |
| TGGTACTCTC | AGTGCCTGTA | AATTTTCGAA | CTTCATCACA | AGCATCCGCC | AAATTCTGTC | 1200 |
| GTCGTCAAAT | CACGCAGGCT | TGGGAACTTT | TTATCTCATG | TCCTGGGCCA | GGACGCAGGA | 1260 |
| GTTAGGACCC | GGATGAGGCC | T | | | | 1281 |

(2) INFORMATION FOR SEQ ID NO: 2:

(i) SEQUENCE CHARACTERISTICS:
    (A) LENGTH: 261 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: Chaetomium thermophilum
    (B) STRAIN: CBS730.95

(ix) FEATURE:
    (A) NAME/KEY: Protein
    (B) LOCATION:1..261
    (D) OTHER INFORMATION:/label= XLNA (xi) SEQUENCE DESCRIPTION: SEQ ID NO: 2:

Met Val Asn Phe Ser Thr Leu Phe Leu Ala Ala Ser Thr Ala Ala Leu

```
1               5                    10                   15
Ala Ala Ala Ala Pro Ser Ile Glu Lys Arg Gln Thr Leu Thr Ser Ser
            20                  25                  30
Ala Thr Gly Thr His Asn Gly Tyr Tyr Ser Phe Trp Thr Asp Gly
        35                  40                  45
Gln Gly Asn Ile Arg Phe Asn Leu Glu Ser Gly Gln Tyr Ser Val
    50                  55                  60
Thr Trp Ser Gly Asn Gly Asn Trp Val Gly Lys Gly Trp Asn Pro
65                  70                  75                  80
Gly Thr Asp Asn Arg Val Ile Asn Tyr Thr Ala Asp Tyr Arg Pro Asn
                85                  90                  95
Gly Asn Ser Tyr Leu Ala Val Tyr Gly Trp Thr Arg Asn Pro Leu Ile
            100                 105                 110
Glu Tyr Tyr Val Val Glu Ser Phe Gly Thr Tyr Asp Pro Ser Thr Gly
            115                 120                 125
Ala Thr Arg Met Gly Ser Val Thr Thr Asp Gly Gly Thr Tyr Asn Ile
    130                 135                 140
Tyr Arg Thr Gln Arg Val Asn Ala Pro Ser Ile Glu Gly Thr Lys Thr
145                 150                 155                 160
Phe Tyr Gln Tyr Trp Ser Val Arg Thr Ser Lys Arg Thr Gly Gly Thr
                165                 170                 175
Val Thr Met Ala Asn His Phe Asn Ala Trp Arg Gln Ala Gly Leu Gln
            180                 185                 190
Leu Gly Ser His Asp Tyr Gln Ile Val Ala Thr Glu Gly Tyr Tyr Ser
        195                 200                 205
Ser Gly Ser Ala Thr Val Asn Val Gly Gly Ser Thr Thr Gly Gly Asn
    210                 215                 220
Asn Gly Gly Asn Asn Gly Gly Asn Asn Gly Gly Asn Asn Gly Gly Asn
225                 230                 235                 240
Thr Gly Ser Asn Val Ser Ile Ser Arg Pro Arg Lys Met Gly Ser Leu
                245                 250                 255
Ala Ser Thr Arg Ser
            260

(2) INFORMATION FOR SEQ ID NO: 3:

(i) SEQUENCE CHARACTERISTICS:
        (A) LENGTH: 1174 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Chaetomium thermophilum
        (B) STRAIN: CBS730.95

(ix) FEATURE:
        (A) NAME/KEY: exon
        (B) LOCATION:204..472
        (D) OTHER INFORMATION:/product= "XLNB"

(ix) FEATURE:
        (A) NAME/KEY: exon
        (B) LOCATION:537..960
        (D) OTHER INFORMATION:/product= "XLNB"

(xi) SEQUENCE DESCRIPTION: SEQ ID NO: 3:

GGGGAGGGTG CCTGATGTTT GTTGCTTATG GATCACTGGG TCGGGATGTA GAAGATATAC    60
```

-continued

```
AACTTAAGGG CGCTGTTATG GCAGCACGAC ATCAAAGTAT ATAAACCGGT AGCCATCTTC      120

CTAGCTCGAG AATCATTGAC CTCACCGTCC AGCTCCCCAC TGCAGTCCTC TCTCCAACCA      180

CAGGACATCA GACAACGATC ACCATGGTCT CCCTCAAATC CCTCCTCCTC ACAGCCGCCA      240

CTGCCCTGGC ATTCCCTCTC GAGGCATTCA ACGCCACCGA GGGTTTCAAT GCCACATCTC      300

TCCACGAGCT GATGGTCCGA GCTGGCACCT CCAGCGGCAC GGGCACACAC AACGGGTGGT      360

ATTACTCCTT CTGGACCGAC GGCGGCGGCA CGGTGTGGTA CACCAATGGT AATGGCGGGT      420

CGTATAGTGT GAACTGGCAG AACTGTGGAA ATTTTGTCGG CGGAAAGGGA TGGTAAGCTC      480

ACTGTCCACC CGGACACTGA AACTTAGTGC CGAGCCAGAT GCTGACCTCT GTCCAGGCGC      540

ACCGGCGCAG CCGCAACGAT CAAATACTCC GGCAACTACA ACCCGTCCGG CAACAGCTAC      600

CTCGCCATCT ACGGCTGGAC GCGCAACCCC CTGGTTGAGT ACTACATCGT CGAGTCGTAC      660

GGCACTTACG ATCCGTCGTC GGGCGCCCAG AACTTGGGCA CATTCCAGTC GGACGGCGGG      720

ACGTACAAGA TCGCCAAGAG CACGCGGTAC AATGCTCCCT CAATCGAAGG AACCAAGACG      780

TTTACGCAGT ATTGGAGCGT GAGGACGTCA AAGCGGGTTG GAGGCACGGT GACGGTTGCG      840

AACCATTTCA ATGCTTGGAA GAGTAAGGGG TTGAATTTGG GTAGCCACGA TTATCAGATT      900

GTGGCGACTG AGGGTTATAA GAGTAGTGGG TCGGCTTCGA TTACTGTTCA GTCTGGTTGA      960

GTGAAGCGAG ATCTGGGGGA GAGAAACAGC GTAGAGGGAT GTCAGGGTTC AAGGTCTGGG     1020

GAACAAGGCT TCACTCACCG AGGTGCGGTC GGGGATGAGC TACTGCAACT TCTGCAGATT     1080

AGCAACTGTT TAGGTAGTTG ATGGGCAGAA TATACCAGTC ATTCTGGAGA TATATATCAT     1140

TGATTTCAAA CCTATATCTG GGACCGGCCT CGAG                                 1174
```

(2) INFORMATION FOR SEQ ID NO: 4:

(i) SEQUENCE CHARACTERISTICS:
        (A) LENGTH: 230 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Chaetomium thermophilum
        (B) STRAIN: CBS730.95

(ix) FEATURE:
        (A) NAME/KEY: Protein
        (B) LOCATION:1..230
        (D) OTHER INFORMATION:/label= XLNB (xi) SEQUENCE DESCRIPTION: SEQ ID NO: 4:

```
Met Val Ser Leu Lys Ser Leu Leu Leu Thr Ala Ala Thr Ala Leu Ala
1               5                   10                  15

Phe Pro Leu Glu Ala Phe Asn Ala Thr Glu Gly Phe Asn Ala Thr Ser
            20                  25                  30

Leu His Glu Leu Met Val Arg Ala Gly Thr Ser Ser Gly Thr Gly Thr
        35                  40                  45

His Asn Gly Trp Tyr Tyr Ser Phe Trp Thr Asp Gly Gly Gly Thr Val
    50                  55                  60

Trp Tyr Thr Asn Gly Asn Gly Gly Ser Tyr Ser Val Asn Trp Gln Asn
65                  70                  75                  80

Cys Gly Asn Phe Val Gly Gly Lys Gly Trp Arg Thr Gly Ala Ala Ala
                85                  90                  95

Thr Ile Lys Tyr Ser Gly Asn Tyr Asn Pro Ser Gly Asn Ser Tyr Leu
```

```
                    100                 105                 110
Ala Ile Tyr Gly Trp Thr Arg Asn Pro Leu Val Glu Tyr Tyr Ile Val
            115                 120                 125

Glu Ser Tyr Gly Thr Tyr Asp Pro Ser Ser Gly Ala Gln Asn Leu Gly
    130                 135                 140

Thr Phe Gln Ser Asp Gly Gly Thr Tyr Lys Ile Ala Lys Ser Thr Arg
145                 150                 155                 160

Tyr Asn Ala Pro Ser Ile Glu Gly Thr Lys Thr Phe Thr Gln Tyr Trp
                165                 170                 175

Ser Val Arg Thr Ser Lys Arg Val Gly Gly Thr Val Thr Val Ala Asn
            180                 185                 190

His Phe Asn Ala Trp Lys Ser Lys Gly Leu Asn Leu Gly Ser His Asp
        195                 200                 205

Tyr Gln Ile Val Ala Thr Glu Gly Tyr Lys Ser Ser Gly Ser Ala Ser
    210                 215                 220

Ile Thr Val Gln Ser Gly
225                 230

(2) INFORMATION FOR SEQ ID NO: 5:

(i) SEQUENCE CHARACTERISTICS:
        (A) LENGTH: 1142 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Chaetomium thermophilum
        (B) STRAIN: CBS730.95

(ix) FEATURE:
        (A) NAME/KEY: exon
        (B) LOCATION:169..425
        (D) OTHER INFORMATION:/product= "XLNC"

(ix) FEATURE:
        (A) NAME/KEY: exon
        (B) LOCATION:500..917
        (D) OTHER INFORMATION:/product= "XLNC"

(xi) SEQUENCE DESCRIPTION: SEQ ID NO: 5:

GGCAGCAGAG ACGTCGGGCT AATGTGTTGA GGTGATGCGA CATGGTGAAA CAGGGGGGGA     60

GATAAAGAG ACTCGACTTT TCTTTAAGCA CAAAAGACAT CACGATCCGT GAAGCCCTAA    120

CTGCACACTA TTGACAAGTT CACCAACGCC ACACTTCCAA TCCTCACAAT GGTCAAACTC    180

GCCCTCCTCA CAACCTCCCT CCTCACCTCT GGCGCCCTCA CCTCCCCAGT CTCAAACCCA    240

AACCGCCCTC CCTCTCGAGA CATCTCCCCC CGCCAATGGG GCGGCGGAGG CTACTACTTC    300

CAAAACTGGT CCGAAGGTGG CAGCAACGTG CGCTGCGTGA ACGCCCAGG CGGGCAATTC    360

AGCGCGACCT GGAACAGCAA GGGTGGGTTC GTGTGCGGTA AGGGCTGGTC GGCGGGTGGT    420

GCACGGTAAC TACATTCCCC CCTCTCCCCC CTTATCCCCT ACCTACCGCC CAACGAAAA    480

CAAGACTAAC GAGCTATAGA GTAATCACCT ACTCCGGCAC CTACAACGCC ACGGGGCCCG    540

GCTACCTCGC CGTCTACGGA TGGACTCGCA ACCCCTTGAT CGAGTACTAC ATCATCGAAG    600

CACATGCCGA ACTTTCCCCC AACGAGCCCT GGACCTACAT GGGTAACTTT TCTTCTCCCG    660

AAGGAGACTA CGACATCTAC ACCAGCTGGC GCATCAATAA GCCGTCGATT GAGGGGACAC    720

GAACGTTCCA ACAGTTCTGG AGCGTGCGAA AGGAACAGAG GGTTAGCGGA ACGGTGACCA    780
```

```
CACAGAGGCA TTTTGATGAG TGGGCTAAGC TGGGGATGCG GCTGGGGAGG CATGATTATG    840

TGGTGATGGC GGTCGAGGGG TATACGGCTG ATGGGGGGTG GGGGAGTGCA GGGGAGGCGA    900

CGATTACGGT GCAGTGAAGG ATTGGATGGG GTGAGTAAGG AACCTGGGTG ATAGGTGAGG    960

CTCCCAGGAT GGGGGAGGAT GGAGGTGGAG GAACTCGACG GGTTTGGGCC CAGTTGAGTC    1020

ACAACAGAGG CAGTTATGGT AGTAGAGAAA TACCAGTACA ATATATTCTA CCAAACCGTG    1080

TTAAGCACGA AAAGTCCCCC TTTGCTGGCA TCGCGGGCCA TCCAGATGTT GCAACCTTCA    1140

GC                                                                   1142
```

(2) INFORMATION FOR SEQ ID NO: 6:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Chaetomium thermophilum
        (B) STRAIN: CBS730.95

(ix) FEATURE:
        (A) NAME/KEY: Protein
        (B) LOCATION:1..224
        (D) OTHER INFORMATION:/label= XLNC (xi) SEQUENCE DESCRIPTION: SEQ ID NO: 6:

```
Met Val Lys Leu Ala Leu Leu Thr Thr Ser Leu Leu Thr Ser Gly Ala
1               5                   10                  15

Leu Thr Ser Pro Val Ser Asn Pro Asn Arg Pro Ser Arg Asp Ile
            20                  25                  30

Ser Pro Arg Gln Trp Gly Gly Gly Tyr Tyr Phe Gln Asn Trp Ser
        35                  40                  45

Glu Gly Gly Ser Asn Val Arg Cys Val Asn Gly Pro Gly Gln Phe
    50                  55                  60

Ser Ala Thr Trp Asn Ser Lys Gly Gly Phe Val Cys Gly Lys Gly Trp
65                  70                  75                  80

Ser Ala Gly Gly Ala Arg Val Ile Thr Tyr Ser Gly Thr Tyr Asn Ala
                85                  90                  95

Thr Gly Pro Gly Tyr Leu Ala Val Tyr Gly Trp Thr Arg Asn Pro Leu
            100                 105                 110

Ile Glu Tyr Tyr Ile Ile Glu Ala His Ala Glu Leu Ser Pro Asn Glu
            115                 120                 125

Pro Trp Thr Tyr Met Gly Asn Phe Ser Ser Pro Glu Gly Asp Tyr Asp
            130                 135                 140

Ile Tyr Thr Ser Trp Arg Ile Asn Lys Pro Ser Ile Glu Gly Thr Arg
145                 150                 155                 160

Thr Phe Gln Gln Phe Trp Ser Val Arg Lys Glu Gln Arg Val Ser Gly
                165                 170                 175

Thr Val Thr Thr Gln Arg His Phe Asp Glu Trp Ala Lys Leu Gly Met
            180                 185                 190

Arg Leu Gly Arg His Asp Tyr Val Val Met Ala Val Glu Gly Tyr Thr
            195                 200                 205

Ala Asp Gly Gly Trp Gly Ser Ala Gly Glu Ala Thr Ile Thr Val Gln
            210                 215                 220
```